(12) United States Patent
Ogawa et al.

(10) Patent No.: US 10,548,868 B2
(45) Date of Patent: *Feb. 4, 2020

(54) METABOLISM-IMPROVING AGENT COMPRISING RARE FATTY ACID

(71) Applicants: KYOTO UNIVERSITY, Kyoto-shi, Kyoto (JP); NITTO PHARMACEUTICAL INDUSTRIES, LTD., Muko-shi, Kyoto (JP)

(72) Inventors: Jun Ogawa, Kyoto (JP); Shigenobu Kishino, Kyoto (JP); Teruo Kawada, Kyoto (JP); Nobuyuki Takahashi, Kyoto (JP); Tsuyoshi Goto, Kyoto (JP); Yasunori Yonejima, Muko (JP)

(73) Assignees: KYOTO UNIVERSITY, Kyoto (JP); NITTO PHARMACEUTICAL INDUSTRIES, LTD., Muko (JP)

(*) Notice: Subject to any disclaimer, the term of this patent is extended or adjusted under 35 U.S.C. 154(b) by 199 days.

This patent is subject to a terminal disclaimer.

(21) Appl. No.: 15/113,654

(22) PCT Filed: Jan. 23, 2015

(86) PCT No.: PCT/JP2015/051843
§ 371 (c)(1),
(2) Date: Jul. 22, 2016

(87) PCT Pub. No.: WO2015/111700
PCT Pub. Date: Jul. 30, 2015

(65) Prior Publication Data
US 2017/0007564 A1    Jan. 12, 2017

(30) Foreign Application Priority Data
Jan. 24, 2014   (JP) ................. 2014-011871

(51) Int. Cl.
*A61K 31/202* (2006.01)
*A61K 31/201* (2006.01)

(52) U.S. Cl.
CPC .......... *A61K 31/202* (2013.01); *A61K 31/201* (2013.01)

(58) Field of Classification Search
None
See application file for complete search history.

(56) References Cited

U.S. PATENT DOCUMENTS

| | | |
|---|---|---|
| 2006/0217441 A1 | 9/2006 | Akimoto et al. |
| 2011/0028538 A1 | 2/2011 | Chang |
| 2015/0125911 A1 | 5/2015 | Ogawa et al. |
| 2015/0342916 A1 | 12/2015 | Ogawa et al. |
| 2016/0000739 A1 | 1/2016 | Ogawa et al. |

FOREIGN PATENT DOCUMENTS

| | | |
|---|---|---|
| JP | 2006-521368 A | 9/2006 |
| JP | 2009-051732 A | 3/2009 |
| JP | 2011-184411 A | 9/2011 |
| WO | WO 2007/090162 A2 | 8/2007 |
| WO | WO 2008/125928 A2 | 10/2008 |
| WO | WO 2009/096579 A1 | 8/2009 |
| WO | WO 2010/039529 A2 | 4/2010 |
| WO | WO 2013/168310 A1 | 11/2013 |
| WO | WO 2014/069227 A1 | 5/2014 |
| WO | WO 2014/129384 A1 | 8/2014 |

OTHER PUBLICATIONS

Kämmerer et al., "13-hydroxy linoleic acid increases expression of the cholesterol transporters ABCA1, ABCG1 and SR-BI and stimulates apoA-I-dependent cholesterol efflux in RAW264.7 macrophages," Lipids in Health and Disease 2011, 10:222.*
Almeida et al., "Increased Lipid Oxidation Causes Oxidative Stress, Increased Peroxisome Proliferator-activated Receptor-γ Expression, and Diminished Pro-osteogenic Wnt Signaling in the Skeleton," *J. Biol. Chem.*, 284(40): 27438-27448 (2009).
Baker et al., "Fatty Acid Transduction of Nitric Oxide Signaling," *J. Biol. Chem.*, 280(51): 42464-42475 (2005).
Fang et al., "14,15-Dihydroxyeicosatrienoic acid activates peroxisome proliferator-activated receptor-α," *Am. J. Physiol. Heart Circ. Physiol.*, 290(1): H55-H63 (2006).
Kammerer et al., "13-hydroxy linoleic acid increases expression of the cholesterol transporters ABCA1, ABCG1 and SR-BI and stimulates apoA-I-dependent cholesterol efflux in RAW264.7 macrophages," *Lipids Health Dis.*, 10: 222 (2011).
Nagy et al., "Oxidized LDL Regulates Macrophage Gene Expression through Ligand Activation of PPARγ," *Cell*, 93(2): 229-240 (1998).
Nakajima et al., "Synthesis of 13-Oxo-(Z)-9-octadecenoic Acid and 15-Oxo-(Z)-11-icosenoic Acid, Arrestants of *Oryzaephilus surinamensis* L.," *Biosci. Biotech. Biochem.*, 61(3): 551-552 (1997).
Naruhn et al., "15-Hydroxyeicosatetraenoic Acid is a Preferential Peroxisome Proliferator-Activated Receptor β/δ Agonist," *Mol. Pharmacol.*, 77(2): 171-184 (2010).
Oh et al., "Biotransformation of Linoleic acid into Hydroxy Fatty Acids and Carboxylic Acids Using a Linoleate Double Bond Hydratase as Key Enzyme," *Adv. Synth. Catal.*, 357(2-3): 408-416 (2015).
Pham et al., "Activation of peroxisome proliferator-activated receptor (PPAR)-gamma by 15S-hydroxyeicosatrienoic acid parallels growth suppression of androgen-dependent prostatic adenocarcinoma cells," *Cancer Lett.*, 189(1): 17-25 (2003).
Shiraki et al., "α,β-Unsaturated Ketone Is a Core Moiety of Natural Ligands for Covalent Binding to Peroxisome Proliferator-activated Receptor γ," *J. Biol. Chem.*, 280(14): 14145-14153 (2005).
Sokmen et al., "Anti-elastase, anti-urease and antioxidant activities of (3-13)-monohydroxyeicosanoic acid isomers," *J. Serb. Chem. Soc.*, 77(10): 1353-1361 (2012).

(Continued)

*Primary Examiner* — Jared Barsky
(74) *Attorney, Agent, or Firm* — Leydig, Voit & Mayer, Ltd.

(57) ABSTRACT

The present invention provides a metabolism improving agent containing a rare fatty acid such as hydroxylated fatty acid, oxo fatty acid and the like, and further, food, pharmaceutical product and the like containing the metabolism improving agent.

12 Claims, 3 Drawing Sheets
Specification includes a Sequence Listing.

(56) References Cited

OTHER PUBLICATIONS

Takahashi et al., "Localization of 9- and 13-oxo-octadecadienoic acids in tomato fruit," *Biosci. Biotechnol. Biochem.*, 78(10): 1761-1764 (2014).
Waku et al., "The nuclear receptor PPARγ individually responds to serotonin- and fatty acid-metabolites," *EMBO J.*, 29(19): 3395-3407 (2010).
Waku et al., "Structural Insight into PPARγ Activation Through Covalent Modification with Endogenous Fatty Acids," *J. Mol. Biol.*, 385(1): 188-199 (2009).
Wauwe et al., "Suggested mechanism for the formation of 15-hydroxyeicosatrienoic acid by rat epidermal microsomes," *Eicosanoids*, 5(3-4): 141-146 (1992).
Kim et al., "9-oxo-10(E),12(E)-octadecadienoic acid derived from tomato is a potent PPARα agonist to decrease triglyceride accumulation in mouse primary hepatocytes," *Mol. Nutr. Food. Res.*, 55(4): 585-593 (2011).
Kim et al., "Potent PPARα Activator Derived from Tomato Juice, 13-oxo-9,11-Octadecadienoic Acid, Decreases Plasma and Hepatic Triglyceride in Obese Diabetic Mice," *PLoS One*, 7(2): e31317 (2012).
Nagao et al., "Conjugated Fatty Acids in Food and Their Health Benefits," *Journal of Bioscience and Bioengineering*, 100(2): 152-157 (2005).
Tanabe et al., "Production of unique hydroxy fatty acid using lactic acid bacteria," *Abstracts of the Annual Conference of the Japan Society for Bioscience, Biotechnology, and Agrochemistry*, 2007: 45, abstract 2A11p13 (2007).
Japanese Patent Office, International Search Report in International Patent Application No. PCT/JP2015/051843 (dated Apr. 21, 2015).
Black et al., "Antifungal Lipids Produced by Lactobacilli and Their Structural Identification by Normal Phase LC/Atmospheric Pressure Photoionization—MS/MS," *J. Agric. Food Chem.*, 61(22): 5338-5346 (2013).
Grechkin et al., "The lipoxygenase pathway in tulip (*Tulipa gesneriana*): detection of the ketol route," *Biochem. J.*, 352(2): 501-509 (2000).
Joo et al., "Biochemical characterization and FAD-binding analysis of oleate hydratase from *Macrococcus caseolyticus*," *Biochimie*, 94(3): 907-915 (2012).
Schuchardt et al., "Comparison of free serum oxylipin concentrations in hyper-vs. normolipidemic men," *Prostaglandins Leukot. Essent. Fatty Acids*, 89(1): 19-29 (2013).
Takeuchi et al., "Hydroxy fatty acid production by *Pediococcus* sp.," *Eur. J. Lipid Sci. Technol.*, 115: 386-393 (2013).
Watanebe et al., "9-Oxooctadeca-10,12-dienoic Acids as Acetyl-CoA Carboxylase Inhibitors from Red Pepper (*Capsicum annuum* L.)," *Biosci. Biotechnol. Biochem.*, 63(3): 489-493 (1999).
Yokoi et al., "Hydroxy Monounsaturated Fatty Acids as Agonists for Peroxisome Proliferator-Activated Receptors," *Biol. Pharm. Bull.*, 33(5): 854-861 (2010).

\* cited by examiner

Fig. 1

| No. | derived fatty acid | abbreviation | structural formula |
|---|---|---|---|
| 1 | Linoleic acid | 13-OH LA | |
| 2 | | 13-OXO LA | |
| 3 | | 10,13-OH LA | |
| 4 | Alpha-linolenic acid | 13-OH ALA | |
| 5 | | 13-OXO ALA | |
| 6 | | 10,13-OH ALA | |
| 7 | Gamma-linolenic acid | 13-OH GLA | |
| 8 | | 13-OXO GLA | |
| 9 | | 10,13-OH GLA | |
| 10 | Arachidonic acid | 15-OH AA | |

…

METABOLISM-IMPROVING AGENT COMPRISING RARE FATTY ACID

CROSS-REFERENCE TO RELATED APPLICATIONS

This patent application is the U.S. national phase of International Patent Application No. PCT/JP2015/051843, filed on Jan. 23, 2015, which claims the benefit of Japanese Patent Application No. 2014-011871, filed Jan. 24, 2014, the disclosures of which are incorporated herein by reference in their entireties for all purposes.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 14,038 bytes ASCII (Text) file named "726079SequenceListing.txt," created Jul. 20, 2016.

TECHNICAL FIELD

The present invention relates to a metabolism improving agent containing a rare fatty acid. More particularly, the present invention relates to a metabolism improving agent utilizing the physiological function, for example, effect of improving metabolism of lipid, sugar and energy, of rare fatty acids such as oxo fatty acid, hydroxy fatty acid and the like. The present invention also relates to a food, a pharmaceutical product, a feed and the like containing the agent.

BACKGROUND ART

In recent years, obesity due to overeating, shortage of exercise and the like, particularly lifestyle-related disease accompanying accumulation of visceral fat, has become a social problem. Metabolic syndrome refers to a condition where at least two of hyperglycemia, hypertension and lipid abnormality are complicated and arteriosclerosis is easily developed due to visceral fat obesity. In Japanese people at the age of 40-74, one in two in male and one in five in female are estimated to have or potentially have metabolic syndrome. Therefore, the importance of adjustment of ingestion calorie by diet therapy with the aim of preventing or solving progress of lipid accumulation in metabolic syndrome has been proposed.

There is considerable interest in ingestion, in dining, of functional lipids reported to have a lipid metabolism improving effect, a diabetes improving effect and the like, including conjugated fatty acids such as conjugated linoleic acid and the like (non-patent document 1), ω3 polyunsaturated fatty acids such as eicosapentaenoic acid, docosahexaenoic acid and the like (patent document 1), medium chain fatty acid (patent document 2) and the like.

In addition, it has been reported in recent years that a part of oxo fatty acids such as 9-oxo-octadecadienoic acid, 13-oxo-octadecadienoic acid and the like contained in tomato have an activity to improve lifestyle-related diseases, such as lipid metabolism improvement and the like (patent document 3, non-patent documents 2, 3). Therefore, the physiological functions of rare fatty acids such as oxo fatty acid, hydroxy fatty acid and the like are also drawing attention.

As regards production of rare fatty acids such as oxo fatty acid, hydroxylated fatty acid and the like, a production method of C10-position hydroxylated fatty acid and C10-position oxo fatty acid, each having 18 carbon atoms, which uses hydration dehydrase derived from *Lactobacillus plantarum*, and which was found by the inventors, has been reported (patent document 4). In addition, a metabolism improving effect (patent document 5), and an intestine protective action (patent document 6) relating to these C10-position hydroxylated fatty acid and C10-position oxo fatty acid have also been reported. However, no report exists as to a suitable production method of hydroxylated fatty acid and oxo fatty acid, each having a carbon atom number other than 18 or hydroxylated fatty acid and oxo fatty acid, each having hydroxyl group, carbonyl group at a position other than C10-position. Moreover, physiological functions of these rare fatty acid derivatives are also unknown.

DOCUMENT LIST

Patent Documents patent document 1: National Publication of International Patent Application No. 2006-521368
patent document 2: Re-published patent No. 2009/096570
patent document 3: JP-A-2011-184411
patent document 4: WO 2013/168310
patent document 5: WO 2014/069227
patent document 6: WO 2014/129384

Non-Patent Document non-patent document 1: Nagao K, (2005), J. Biosci. Bioeng., vol. 100, no. 2, p. 152-157
non-patent document 2: Kim Y-I, (2011), Mol. Nutr. Food Res., vol. 55, p. 585-593
non-patent document 3: Kim Y-I, (2012), PLoS ONE, vol. 7, no. 2, e31317

SUMMARY OF THE INVENTION

Problems to be Solved by the Invention

An object of the present invention is to provide a novel metabolism improving agent containing a rare fatty acid, which improves the metabolism of lipid and/or sugar and the like.

Means of Solving the Problems

The present inventors have conducted intensive studies in view of the above-mentioned problems and found that a hydroxylated fatty acid, for example, 13-hydroxy-cis-9-octadecenoic acid, or an oxo fatty acid, for example, 13-oxo-cis-9-octadecenoic acid has a peroxisome proliferator-activated receptor (hereinafter to be also referred to as "PPAR")-activating action, which is a conventionally-unknown physiological function.

The present invention was completed based on the above findings.

Accordingly, the present invention provides the following:

[1] A metabolism improving agent comprising the following fatty acid:
(1) a fatty acid having 18 carbon atoms and a hydroxyl group or carbonyl group at the 13-position,
(2) a fatty acid having 20 carbon atoms and a hydroxyl group or carbonyl group at the 15-position, (3) a fatty acid having 20 carbon atoms and a hydroxyl group or carbonyl group at the 12-position,
(4) a fatty acid having 16 carbon atoms and a hydroxyl group or carbonyl group at the 10-position;
[2] the agent of [1], comprising the following fatty acid:
(1) a saturated fatty acid or an unsaturated fatty acid having at least one cis double bond at the 6-position, the 9-position, the 15-position, which has 18 carbon atoms and a hydroxyl group or carbonyl group at the 13-position,
(2) an unsaturated fatty acid having at least one cis double bond at the 5-position, the 8-position, the 11-position, the 17-position, which has 20 carbon atoms and a hydroxyl group or carbonyl group at the 15-position, and,
(3) a saturated fatty acid or an unsaturated fatty acid having at least one cis double bond at the 5-position, the 8-position, the 14-position, the 17-position, which has 20 carbon atoms and a hydroxyl group or carbonyl group at the 12-position, or
(4) a saturated fatty acid having 16 carbon atoms and a hydroxyl group or carbonyl group at the 10-position;
[3] the agent of [2], comprising the following fatty acid:
(1) a saturated fatty acid or an unsaturated fatty acid having at least one cis double bond at the 6-position, the 9-position, the 15-position, which has 18 carbon atoms and a hydroxyl group or carbonyl group at the 13-position, or
(2) an unsaturated fatty acid having at least one cis double bond at the 5-position, the 8-position, the 11-position, the 17-position, which has 20 carbon atoms and a hydroxyl group or carbonyl group at the 15-position;
[4] the agent of [2], wherein
(1) the saturated fatty acid or the saturated fatty acid having at least one cis double bond at the 6-position, the 9-position, the 15-position, which has 18 carbon atoms and a hydroxyl group or carbonyl group at the 13-position, is 13-hydroxy-cis-9-octadecenoic acid, 13-hydroxy-cis-6,cis-9-octadecadienoic acid, 13-hydroxy-cis-9,cis-15-octadecadienoic acid, 13-hydroxy-cis-6,cis-9,cis-15-octadecatrienoic acid, 10,13-dihydroxy-octadecanoic acid, 10,13-dihydroxy-cis-6-octadecenoic acid, 10,13-dihydroxy-cis-15-octadecenoic acid, 10,13-dihydroxy-cis-6,cis-15-octadecadienoic acid, 10-oxo-13-hydroxy-octadecanoic acid, 10-oxo-13-hydroxy-cis-6-octadecenoic acid, 10-oxo-13-hydroxy-cis-15-octadecenoic acid, 10-oxo-13-hydroxy-cis-6,cis-15-octadecadienoic acid, 13-hydroxy-cis-5,cis-9-octadecadienoic acid, 13-hydroxy-trans-5,cis-9-octadecadienoic acid, 13-oxo-cis-9-octadecenoic acid, 13-oxo-cis-6,cis-9-octadecadienoic acid, 13-oxo-cis-9,cis-15-octadecadienoic acid, 13-oxo-cis-6,cis-9,cis-15-octadecatrienoic acid, 10,13-dioxo-octadecanoic acid, 10,13-dioxo-cis-6-octadecenoic acid, 10,13-dioxo-cis-15-octadecenoic acid, 10,13-dioxo-cis-6,cis-15-octadecadienoic acid, 13-oxo-cis-5,cis-9-octadecadienoic acid or 13-oxo-trans-5,cis-9-octadecadienoic acid,
(2) the unsaturated fatty acid having at least one cis double bond at the 5-position, the 8-position, the 11-position, the 17-position, which has 20 carbon atoms and a hydroxyl group or carbonyl group at the 15-position, is 15-hydroxy-cis-11-eicosenoic acid, 15-hydroxy-cis-11,cis-17-eicosadienoic acid, 15-hydroxy-cis-8,cis-11-eicosadienoic acid, 15-hydroxy-cis-5,cis-8,cis-11-eicosatrienoic acid, 15-hydroxy-cis-8,cis-11,cis-17-eicosatrienoic acid, 15-hydroxy-cis-5,cis-11-eicosadienoic acid, 15-hydroxy-cis-5,cis-11,cis-17-eicosatrienoic acid, 15-oxo-cis-11-eicosenoic acid, 15-oxo-cis-11,cis-17-eicosadienoic acid, 15-oxo-cis-8,cis-11-eicosadienoic acid, 15-oxo-cis-5,cis-8,cis-11-eicosatrienoic acid, 15-oxo-cis-8,cis-11,cis-17-eicosatrienoic acid, 15-oxo-cis-5,cis-11-eicosadienoic acid or 15-oxo-cis-5,cis-11,cis-17-eicosatrienoic acid, (3) the saturated fatty acid or the unsaturated fatty acid having at least one cis double bond at the 5-position, the 8-position, the 14-position, the 17-position, which has 20 carbon atoms and a hydroxyl group or carbonyl group at the 12-position, is 12-hydroxy-cis-14-eicosenoic acid, 12-hydroxy-cis-14,cis-17-eicosadienoic acid, 12-hydroxy-cis-8,cis-14-eicosadienoic acid, 12-hydroxy-cis-5,cis-8-eicosadienoic acid, 12-hydroxy-cis-8,cis-14,cis-17-eicosatrienoic acid, 12-hydroxy-cis-5,cis-8,cis-14-eicosatrienoic acid, 12-oxo-cis-14-eicosenoic acid, 12-oxo-cis-14,cis-17-eicosadienoic acid, 12-oxo-cis-8,cis-14-eicosadienoic acid, 12-oxo-cis-5,cis-8-eicosadienoic acid, 12-oxo-cis-8,cis-14,cis-17-eicosatrienoic acid, or 12-oxo-cis-5,cis-8, cis-14-eicosatrienoic acid, and
(4) the saturated fatty acid having 16 carbon atoms and a hydroxyl group or carbonyl group at the 10-position is 10-hydroxy-hexadecanoic acid or 10-oxo-hexadecanoic acid;
[5] the agent of [3], wherein
(1) the saturated fatty acid or the unsaturated fatty acid having at least one cis double bond at the 6-position, the 9-position, the 15-position, which has 18 carbon atoms and a hydroxyl group or carbonyl group at the 13-position, is 13-hydroxy-cis-9-octadecenoic acid, 13-hydroxy-cis-6,cis-9-octadecadienoic acid, 13-hydroxy-cis-9,cis-15-octadecadienoic acid, 10,13-dihydroxy-octadecanoic acid, 10,13-dihydroxy-cis-6-octadecenoic acid, 10,13-dihydroxy-cis-15-octadecenoic acid, 13-oxo-cis-9-octadecenoic acid, 13-oxo-cis-6,cis-9-octadecadienoic acid, or 13-oxo-cis-9,cis-15-octadecadienoic acid, and
(2) the unsaturated fatty acid having at least one cis double bond at the 5-position, the 8-position, the 11-position, the 17-position, which has 20 carbon atoms and a hydroxyl group or carbonyl group at the 15-position, is 15-hydroxy-cis-5,cis-8,cis-11-eicosatrienoic acid;
[6] The agent of any one of [1]-[5], which is used for the prophylaxis or improvement of at least one kind selected from the group consisting of obesity, diabetes, lipid metabolism abnormality, hyperlipidemia, and fatty liver.
[7] The agent of any one of [1]-[5], which is a food or a food additive.
[8] The agent of any one of [1]-[5], which is a pharmaceutical product.
[9] The agent of any one of [1]-[5], which is a feed or a feed additive.
[10] a PPAR activity promoter comprising the following fatty acid:
(1) a fatty acid having 18 carbon atoms and a hydroxyl group or 10 carbonyl group at the 13-position,
(2) a fatty acid having 20 carbon atoms and a hydroxyl group or carbonyl group at the 15-position,
(3) a fatty acid having 20 carbon atoms and a hydroxyl group or carbonyl group at the 12-position,
(4) a fatty acid having 16 carbon atoms and a hydroxyl group or carbonyl group at the 10-position;
[11] the promoter of [10], comprising the following fatty acid:
(1) a saturated fatty acid or an unsaturated fatty acid having at least one cis double bond at the 6-position, the 9-position, the 15-position, which has 18 carbon atoms and a hydroxyl group or carbonyl group at the 13-position,
(2) an unsaturated fatty acid having at least one cis double bond at the 5-position, the 8-position, the 11-position, the 17-position, which has 20 carbon atoms and a hydroxyl group or carbonyl group at the 15-position,
(3) a saturated fatty acid or an unsaturated fatty acid having at least one cis double bond at the 5-position, the 8-position, the 14-position, the 17-position, which has 20 carbon atoms and a hydroxyl group or carbonyl group at the 12-position, or (4) a saturated fatty acid having 16 carbon atoms and a hydroxyl group or carbonyl group at the 10-position;

[12] the promoter of [11], comprising the following fatty acid:

(1) a saturated fatty acid or an unsaturated fatty acid having at least one cis double bond at the 6-position, the 9-position, the 15-position, which has 18 carbon atoms and a hydroxyl group or carbonyl group at the 13-position, or (2) an unsaturated fatty acid having at least one cis double bond at the 5-position, the 8-position, the 11-position, the 17-position, which has 20 carbon atoms and a hydroxyl group or carbonyl group at the 15-position;

[13] the promoter of [11], wherein (1) the saturated fatty acid or the saturated fatty acid having at least one cis double bond at the 6-position, the 9-position, the 15-position, which has 18 carbon atoms and a hydroxyl group or carbonyl group at the 13-position, is 13-hydroxy-cis-9-octadecenoic acid, 13-hydroxy-cis-6,cis-9-octadecadienoic acid, 13-hydroxy-cis-9,cis-15-octadecadienoic acid, 13-hydroxy-cis-6,cis-9,cis-15-octadecatrienoic acid, 10,13-dihydroxy-octadecanoic acid, 10,13-dihydroxy-cis-6-octadecenoic acid, 10,13-dihydroxy-cis-15-octadecenoic acid, 10,13-dihydroxy-cis-6,cis-15-octadecadienoic acid, 10-oxo-13-hydroxy-octadecanoic acid, 10-oxo-13-hydroxy-cis-6-octadecenoic acid, 10-oxo-13-hydroxy-cis-15-octadecenoic acid, 10-oxo-13-hydroxy-cis-6,cis-15-octadecadienoic acid, 13-hydroxy-cis-5,cis-9-octadecadienoic acid, 13-hydroxy-trans-5,cis-9-octadecadienoic acid, 13-oxo-cis-9-octadecenoic acid, 13-oxo-cis-6,cis-9-octadecadienoic acid, 13-oxo-cis-9,cis-15-octadecadienoic acid, 13-oxo-cis-6,cis-9,cis-15-octadecatrienoic acid, 10,13-dioxo-octadecanoic acid, 10,13-dioxo-cis-6-octadecenoic acid, 10,13-dioxo-cis-15-octadecenoic acid, 10,13-dioxo-cis-6,cis-15-octadecadienoic acid, 13-oxo-cis-5,cis-9-octadecadienoic acid or 13-oxo-trans-5,cis-9-octadecadienoic acid, (2) the unsaturated fatty acid having at least one cis double bond at the 5-position, the 8-position, the 11-position, the 17-position, which has 20 carbon atoms and a hydroxyl group or carbonyl group at the 15-position, is 15-hydroxy-cis-11-eicosenoic acid, 15-hydroxy-cis-11,cis-17-eicosadienoic acid, 15-hydroxy-cis-8,cis-11-eicosadienoic acid, 15-hydroxy-cis-5,cis-8,cis-11-eicosatrienoic acid, 15-hydroxy-cis-8,cis-11,cis-17-eicosatrienoic acid, 15-hydroxy-cis-5,cis-11-eicosadienoic acid, 15-hydroxy-cis-5,cis-11,cis-17-eicosatrienoic acid, 15-oxo-cis-11-eicosenoic acid, 15-oxo-cis-11,cis-17-eicosadienoic acid, 15-oxo-cis-8,cis-11-eicosadienoic acid, 15-oxo-cis-5,cis-8,cis-11-eicosatrienoic acid, 15-oxo-cis-8,cis-11,cis-17-eicosatrienoic acid, 15-oxo-cis-5,cis-11-eicosadienoic acid or 15-oxo-cis-5,cis-11,cis-17-eicosatrienoic acid, (3) the saturated fatty acid or the unsaturated fatty acid having at least one cis double bond at the 5-position, the 8-position, the 14-position, the 17-position, which has 20 carbon atoms and a hydroxyl group or carbonyl group at the 12-position, is 12-hydroxy-cis-14-eicosenoic acid, 12-hydroxy-cis-14,cis-17-eicosadienoic acid, 12-hydroxy-cis-8,cis-14-eicosadienoic acid, 12-hydroxy-cis-5,cis-8-eicosadienoic acid, 12-hydroxy-cis-8,cis-14,cis-17-eicosatrienoic acid, 12-hydroxy-cis-5,cis-8,cis-14-eicosatrienoic acid, 12-oxo-cis-14-eicosenoic acid, 12-oxo-cis-14,cis-17-eicosadienoic acid, 12-oxo-cis-8,cis-14-eicosadienoic acid, 12-oxo-cis-5,cis-8-eicosadienoic acid, 12-oxo-cis-8,cis-14,cis-17-eicosatrienoic acid, or 12-oxo-cis-5,cis-8,cis-14-eicosatrienoic acid, and (4) the saturated fatty acid having 16 carbon atoms and a hydroxyl group or carbonyl group at the 10-position is 10-hydroxy-hexadecanoic acid or 10-oxo-hexadecanoic acid;

[14] the promoter of [12], wherein (1) the saturated fatty acid or the unsaturated fatty acid having at least one cis double bond at the 6-position, the 9-position, the 15-position, which has 18 carbon atoms and a hydroxyl group or carbonyl group at the 13-position, is 13-hydroxy-cis-9-octadecenoic acid, 13-hydroxy-cis-6, cis-9-octadecadienoic acid, 13-hydroxy-cis-9,cis-15-octadecadienoic acid, 10,13-dihydroxy-octadecanoic acid, 10,13-dihydroxy-cis-6-octadecenoic acid, 10,13-dihydroxy-cis-15-octadecenoic acid, 13-oxo-cis-9-octadecenoic acid, 13-oxo-cis-6, cis-9-octadecadienoic acid, or 13-oxo-cis-9,cis-15-octadecadienoic acid, and (2) the unsaturated fatty acid having at least one cis double bond at the 5-position, the 8-position, the 11-position, the 17-position, which has 20 carbon atoms and a hydroxyl group or carbonyl group at the 15-position, is 15-hydroxy-cis-5,cis-8,cis-11-eicosatrienoic acid;

[15] the promoter of any one of [10]-[14], wherein the PPAR is PPARα or PPARγ;

[16] a method for the prophylaxis or treatment of a disease relating to metabolism, comprising administering an effective amount of the fatty acid of any one of [1]-[5] to a patient;

[17] the method of [16], wherein the disease relating to metabolism is at least one kind selected from the group consisting of obesity, diabetes, lipid metabolism abnormality, hyperlipidemia, and fatty liver;

[18] the fatty acid of any one of [1]-[5] for use for the prophylaxis or treatment of a disease relating to metabolism;

[19] the fatty acid of [18], wherein the disease relating metabolism is at least one kind selected from the group consisting of obesity, diabetes, lipid metabolism abnormality, hyperlipidemia, and fatty liver;

[20] use of the fatty acid of any one of [1]-[5] in producing a prophylactic or therapeutic agent for a disease relating metabolism;

[21] the use of [20], wherein the disease relating metabolism is at least one kind is selected from the group consisting of obesity, diabetes, lipid metabolism abnormality, hyperlipidemia, and fatty liver.

Effect of the Invention

In the present invention, it was found that hydroxylated fatty acid or oxo fatty acids such as 13-hydroxy-cis-9-octadecenoic acid and 13-oxo-cis-9-octadecenoic acid (hereinafter to be also referred to as hydroxylated fatty acid and the like) have a PPAR activation action which is a physiological function not conventionally known.

Based on such functions, the present invention provides a metabolism improving agent containing rare fatty acid such as the above-mentioned hydroxylated fatty acid and the like. Since the agent can be used in various fields such as pharmaceutical product, food, feed and the like, the present invention is industrially extremely useful.

BRIEF DESCRIPTION OF THE DRAWINGS

FIG. 1 shows structural formulas of hydroxylated fatty acid and oxo fatty acid measured for the PPARα/γ agonist activity.

DESCRIPTION OF EMBODIMENTS

Figure 2:
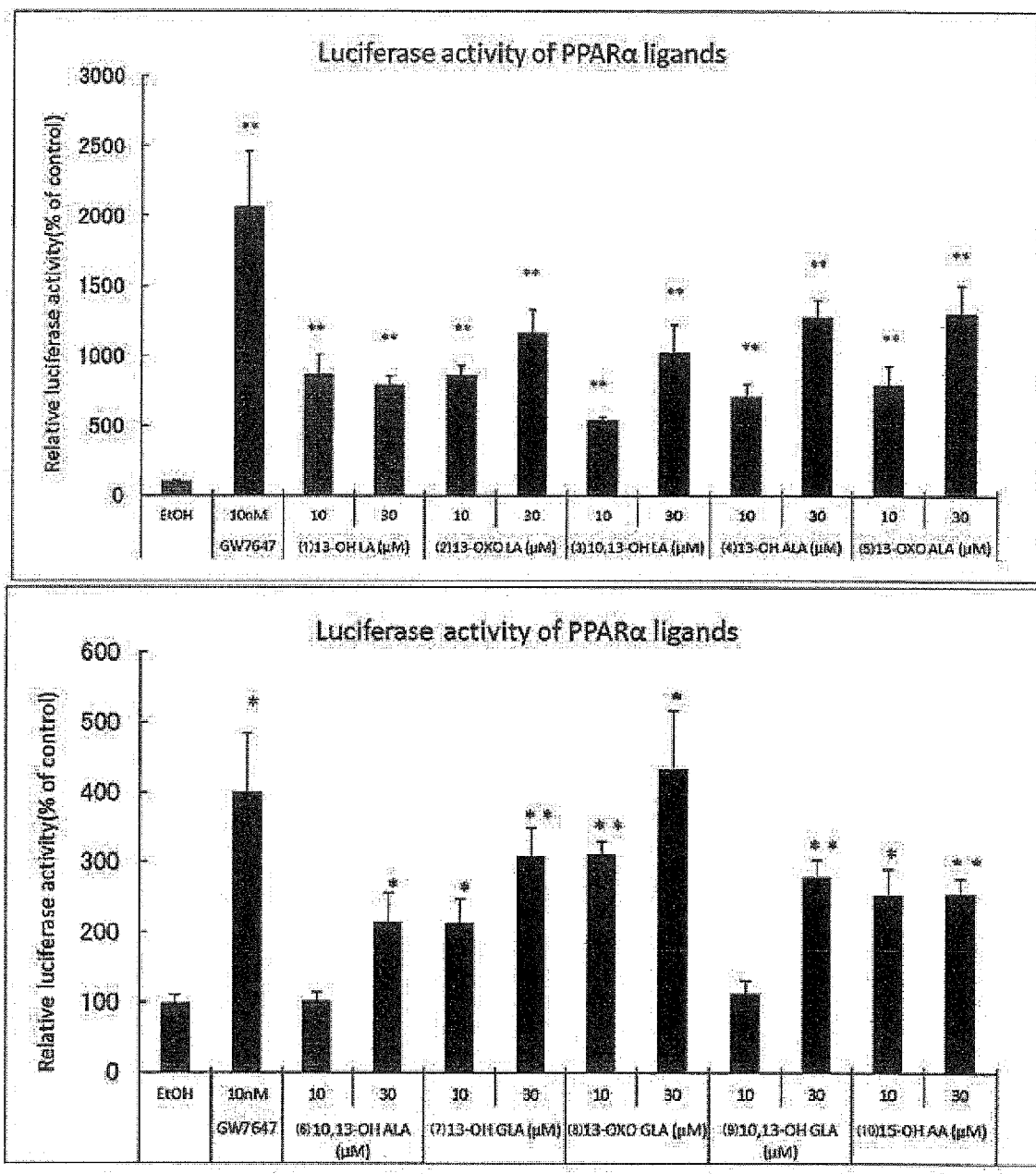
FIG. 2 shows the results of PPARα agonist activity of hydroxylated fatty acid and oxo fatty acid, wherein EtOH shows negative control (ethanol addition), GW7647 shows positive control (PPARα agonist addition), and the vertical axis shows relative luciferase activity.

The present invention is explained in detail below.

In the present invention, the "metabolism improvement" means that the metabolism of lipid and/or sugar and/or energy are/is improved. Specifically, for example, lipid metabolism improvement means promotion of the decomposition of lipid present in the body tissue, blood, or lymph tissue, suppression of lipid synthesis, prevention and/or suppression of accumulation of lipid in body tissues such as adipose tissue and the like, or reduction of lipid accumulated in body tissue and the like. The "lipid" is triglyceride and/or cholesterol, including fatty acid.

The improvement of sugar metabolism means suppression of an increase in sugar, and/or glycated hemoglobin (HbA1c) present in blood, fasting blood sugar level, or promotion of sugar metabolism after eating. Furthermore, sugar metabolism improvement also includes improvement of impaired glucose tolerance (pathology not included in normal type or diabetes type, and pre-diabetic). The "sugar" refers to monosaccharide, disaccharide or polysaccharide.

The improvement of energy metabolism means bringing the state of abnormal balance of ingested energy level and release energy level, or the state of unattainable control of the balance of ingested energy level and release energy level, to a normal state or closer to a normal state.

As an index of the aforementioned metabolism improvement, PPAR activity can be measured. It is known that PPAR includes at least 3 kinds of subtypes: PPARα, PPARδ (same as β) and PPARγ. PPARα is mainly expressed in the liver, heart, kidney, skeletal muscle, brown adipocyte and the like, and is involved in control of many genes relating to β oxidation of fatty acid. PPARδ is expressed in comparatively all over the body (brain, adipose tissue, skin etc.). PPARγ has at least 3 kinds of isoforms, is mainly expressed in white adipocyte and macrophage, and is involved in adipocyte differentiation and the like. When the presence or absence of a ligand (agonist, antagonist) activity is confirmed for at least one kind of PPAR from these PPARs and an agonist activity is found, it is judged that the possibility of having a metabolism improving effect is high, or a metabolism improving effect is present. As one example, the PPAR reporter assay described in FEES Letters 514 (2002) p. 315-322 can be performed. However, the method is not limited thereto.

Alternatively, as an index of metabolism improvement, of the rare fatty acid of the present invention may be administered to obesity or diabetes animal model, body weight, organ weight, blood glucose level, neutral fats value, oxygen consumption level, rectal temperature and the like are measured, and the presence or absence of the changes thereof can be confirmed. The obesity or diabetes animal model is not limited as long as it is an animal showing the properties. For example, as the aforementioned animal model, commercially available KKAy mouse, NOD mouse, NSY mouse, TSOD mouse, ZDF/Crl-Leprfa rat, SDT/Jcl rat and the like can be recited. The body weight, organ weight, blood glucose level, neutral fats value, oxygen consumption level, rectal temperature and the like can be measured by a known method. Using these as indices, when a decrease in the body weight or organ weight, or blood glucose level, neutral fats value is observed, or when an increase in the oxygen consumption level or rectal temperature is observed, it is judged that the possibility of having a metabolism improving effect is high, or a metabolism improving effect is present.

Alternatively, as an index of metabolism improvement, whether a lipid synthesis-promoting action induced by LXR agonist is suppressed by the addition of the rare fatty acid of the present invention can be confirmed. As a method therefor, for example, Journal of Lipid Research 47 (2006) 2712-2717 can be referred to, but the method is not limited thereto. The method described in the aforementioned document includes adding a LXR agonist, and (1) measuring the expression level of mRNA and/or protein of lipid synthesis-related factors, for example, SREBP-1c, mature and immature SREBP-1, SCD-1, FAS, ACC1 and/or ACC2, (2) measuring an intracellular triacylglycerol level, or (3) performing luciferase assay. Examples of the LXR agonist include, but are not limited to, T0901317, 22(R)-hydroxycholesterol, 24(S)-hydroxycholesterol and the like. When the expression level of mRNA and/or protein of lipid synthesis-related factor decreases, it is judged that the lipid synthesis is suppressed, and the possibility of having a metabolism improving effect is high, or a metabolism improving effect is present.

In the present invention, a fatty acid having 18 carbon atoms and a hydroxyl group or carbonyl group at the 13-position refers to a hydroxylated fatty acid having 18 carbon atoms and a hydroxyl group at the 13-position (hereinafter sometimes to be abbreviated as "13-hydroxy fatty acid"), or an oxo fatty acid having 18 carbon atoms and a carbonyl group at the 13-position (hereinafter sometimes to be abbreviated as "13-oxo fatty acid"). As used herein, a fatty acid having 18 carbon atoms and a hydroxyl group or carbonyl group at the 10-position and the 13-position (hereinafter sometimes to be abbreviated as "10,13-dihydroxy fatty acid" or "10,13-dioxo fatty acid"), and a fatty acid having 18 carbon atoms and a hydroxyl group at the 13-position and a carbonyl group at the 10-position (hereinafter sometimes to be abbreviated as "10-oxo-13-hydroxy fatty acid") are also encompassed in one embodiment of the "13-hydroxy fatty acid" or "13-oxo fatty acid". In addition, the fatty acid having 18 carbon atoms and a hydroxyl group or carbonyl group at the 13-position may be a saturated fatty acid or an unsaturated fatty acid. When it is an unsaturated fatty acid, an unsaturated fatty acid having at least one cis double bond at the 6-position, the 9-position and the 15-position is preferable.

In the present invention, the fatty acid having 20 carbon atoms and a hydroxyl group or carbonyl group at the 15-position refers to a hydroxylated fatty acid having 20 carbon atoms and a hydroxyl group at the 15-position (hereinafter sometimes to be abbreviated as "15-hydroxy fatty acid"), or oxo fatty acid having 20 carbon atoms and a carbonyl group at the 15-position fatty acid (hereinafter sometimes to be abbreviated as "15-oxo fatty acid"). In addition, the fatty acid having 20 carbon atoms and a hydroxyl group or carbonyl group at the 15-position may be a saturated fatty acid or an unsaturated fatty acid. When it is an unsaturated fatty acid, an unsaturated fatty acid having at least one cis double bond at the 5-position, the 8-position, the 11-position, the 17-position is preferable.

In the present invention, the fatty acid having 20 carbon atoms and a hydroxyl group or carbonyl group at the 12-position refers to a hydroxylated fatty acid having 20 carbon atoms and a hydroxyl group at the 12-position (hereinafter sometimes to be abbreviated as "12-hydroxy fatty acid"), or oxo fatty acid having 20 carbon atoms and a carbonyl group at the 12-position (hereinafter sometimes to be abbreviated as "12-oxo fatty acid"). In addition, the fatty acid having 20 carbon atoms and a hydroxyl group or carbonyl group at the 12-position may be a saturated fatty acid or an unsaturated fatty acid. When it is an unsaturated fatty acid, an unsaturated fatty acid having at least one cis double bond at the 5-position, the 8-position, the 14-position, the 17-position is preferable.

In the present invention, the fatty acid having 16 carbon atoms and a hydroxyl group or carbonyl group at the 10-position refers to a hydroxylated fatty acid having 16 carbon atoms and a hydroxyl group at the 10-position (hereinafter sometimes to be abbreviated as "10-hydroxy fatty acid"), or oxo fatty acid having 16 carbon atoms and a carbonyl group at the 10-position (hereinafter sometimes to be abbreviated as "10-oxo fatty acid"). In addition, the fatty acid having 16 carbon atoms and a hydroxyl group or carbonyl group at the 10-position may be a saturated fatty acid or an unsaturated fatty acid.

More specifically, while the saturated fatty acid or the unsaturated fatty acid having at least one cis double bond at the 6-position, 9-position, the 15-position, which has 18 carbon atoms and a hydroxyl group or carbonyl group at the 13-position, is not particularly limited, 13-hydroxy-cis-9-octadecenoic acid, 13-hydroxy-cis-6,cis-9-octadecadienoic acid, 13-hydroxy-cis-9,cis-15-octadecadienoic acid, 13-hydroxy-cis-6,cis-9,cis-15-octadecatrienoic acid, 10,13-dihydroxy-octadecanoic acid, 10,13-dihydroxy-cis-6-octadecenoic acid, 10,13-dihydroxy-cis-15-octadecenoic acid, 10,13-dihydroxy-cis-6,cis-15-octadecadienoic acid, 10-oxo-13-hydroxy-octadecanoic acid, 10-oxo-13-hydroxy-cis-6-octadecenoic acid, 10-oxo-13-hydroxy-cis-15-octadecenoic acid, 10-oxo-13-hydroxy-cis-6,cis-15-octadecadienoic acid, 13-hydroxy-cis-5,cis-9-octadecadienoic acid, 13-hydroxy-trans-5,cis-9-octadecadienoic acid, 13-oxo-cis-9-octadecenoic acid, 13-oxo-cis-6,cis-9-octadecadienoic acid, 13-oxo-cis-9,cis-15-octadecadienoic acid, 13-oxo-cis-6,cis-9,cis-15-octadecatrienoic acid, 10,13-dioxo-octadecanoic acid, 10,13-dioxo-cis-6-octadecenoic acid, 10,13-dioxo-cis-15-octadecenoic acid, 10,13-dioxo-cis-6,cis-15-octadecadienoic acid, 13-oxo-cis-5,cis-9-octadecadienoic acid or 13-oxo-trans-5,cis-9-octadecadienoic acid and the like can be mentioned; more preferably, 13-hydroxy-cis-9-octadecenoic acid, 13-hydroxy-cis-6,cis-9-octadecadienoic acid, 13-hydroxy-cis-9,cis-15-octadecadienoic acid, 10,13-dihydroxy-octadecanoic acid, 10,13-dihydroxy-cis-6-octadecenoic acid, 10,13-dihydroxy-cis-15-octadecenoic acid, 13-oxo-cis-9-octadecenoic acid, 13-oxo-cis-6,cis-9-octadecadienoic acid, or 13-oxo-cis-9,cis-15-octadecadienoic acid can be mentioned.

While the unsaturated fatty acid having at least one cis double bond at the 5-position, the 8-position, the 11-position, the 17-position, which has 20 carbon atoms and a hydroxyl group or carbonyl group at the 15-position, is not particularly limited, 15-hydroxy-cis-11-eicosenoic acid, 15-hydroxy-cis-11,cis-17-eicosadienoic acid, 15-hydroxy-cis-8,cis-11-eicosadienoic acid, 15-hydroxy-cis-5,cis-8,cis-11-eicosatrienoic acid, 15-hydroxy-cis-8,cis-11,cis-17-eicosatrienoic acid, 15-hydroxy-cis-5,cis-11-eicosadienoic acid, 15-hydroxy-cis-5,cis-11,cis-17-eicosatrienoic acid, 15-oxo-cis-11-eicosenoic acid, 15-oxo-cis-11,cis-17-eicosadienoic acid, 15-oxo-cis-8,cis-11-eicosadienoic acid, 15-oxo-cis-5,cis-8,cis-11-eicosatrienoic acid, 15-oxo-cis-8, cis-11,cis-17-eicosatrienoic acid, 15-oxo-cis-5,cis-11-eicosadienoic acid or 15-oxo-cis-5,cis-11,cis-17-eicosatrienoic acid and the like can be mentioned; more preferably, 15-hydroxy-cis-5,cis-8,cis-11-eicosatrienoic acid can be mentioned.

While the saturated fatty acid or the unsaturated fatty acid least one cis double bond the 5-position, the 8-position, the 14-position, the 17-position, which has 20 carbon atoms and a hydroxyl group or carbonyl group at the 12-position, is not particularly limited, 12-hydroxy-cis-14-eicosenoic acid, 12-hydroxy-cis-14,cis-17-eicosadienoic acid, 12-hydroxy-cis-8,cis-14-eicosadienoic acid, 12-hydroxy-cis-5,cis-8-eicosadienoic acid, 12-hydroxy-cis-8,cis-14,cis-17-eicosatrienoic acid, 12-hydroxy-cis-5,cis-8,cis-14-eicosatrienoic acid, 12-oxo-cis-14-eicosenoic acid, 12-oxo-cis-14,cis-17-eicosadienoic acid, 12-oxo-cis-8,cis-14-eicosadienoic acid, 12-oxo-cis-5,cis-8-eicosadienoic acid, 12-oxo-cis-8,cis-14,cis-17-eicosatrienoic acid, or 12-oxo-cis-5,cis-8,cis-14-eicosatrienoic acid and the like can be mentioned.

While the saturated fatty acid having 16 carbon atoms and a hydroxyl group or carbonyl group at the 10-position is not particularly limited, 10-hydroxy-hexadecanoic acid or 10-oxo-hexadecanoic acid and the like can be mentioned.

As the rare fatty acids such as oxo fatty acid, hydroxylated fatty acid and the like to be used in the present invention, a hydroxylated fatty acid is produced from an unsaturated fatty acid having 16, 18, 20 carbon atoms by a novel fatty acid hydration enzyme (FA-HY), and an oxo fatty acid can be produced by further oxidizing the hydroxyl group of the hydroxylated fatty acid by an enzyme reaction or chemical reaction. Specifically, it can be prepared by the following method.

The aforementioned novel fatty acid hydration enzyme "FA-HY" is (a) the enzyme protein consisting of the amino acid sequence shown in SEQ ID NO: 2, (b) a protein comprising an amino acid sequence wherein one or plural amino acids in the amino acid sequence shown in SEQ ID NO: 2 are deleted and/or substituted and/or inserted and/or added, and having an enzyme activity that the enzyme protein consisting of the amino acid sequence shown in SEQ ID NO: 2 has, or (c) a protein encoded by a base sequence that hybridizes to a nucleic acid consisting of a chain sequence complementary to the base sequence shown in SEQ ID NO: 1 under stringent conditions, and having an enzyme activity that the enzyme protein consisting of the amino acid sequence shown in SEQ ID NO: 2 has.

More specific examples of the above-mentioned (b) include a protein containing (i) an amino acid sequence which is the amino acid sequence shown in SEQ ID NO: 2, wherein 1-20, preferably 1-10, more preferably 1-several (5, 4, 3 or 2) amino acids are deleted, (ii) an amino acid sequence which is the amino acid sequence shown in SEQ ID NO: 2, wherein 1-20, preferably 1-10, more preferably 1-several number (5, 4, 3 or 2) amino acids are added, (iii) an amino acid sequence which is the amino acid sequence shown in SEQ ID NO: 2, wherein 1-20, preferably 1-10, more preferably 1-several (5, 4, 3 or 2) amino acids are inserted, (iv) an amino acid sequence which is the amino acid sequence shown in SEQ ID NO: 2, wherein 1-20, preferably 1-10, more preferably 1-several (5, 4, 3 or 2) amino acids are substituted by other amino acids, or (v) an amino acid sequence obtained by combining them. When amino acids with similar properties (e.g., glycine and alanine, valine and leucine and isoleucine, serine and threonine, aspartic acid and glutamic acid, asparagine and glutamine, lysine and arginine, cysteine and methionine, phenylalanine and tyrosine etc.) are substituted with each other and the like, a greater number of substitutions and the like are possible.

When amino acids are deleted, substituted or inserted as mentioned above, the positions of deletion, substitution and insertion are not particularly limited as long as the above-mentioned enzyme activity is maintained.

In the above-mentioned (c), the "stringent conditions" are conditions under which nucleotide sequences having high identity, for example, identity of 70, 80, 90, 95 or 99% or above, hybridize to each other and nucleotide sequences having identity lower than that do not hybridize; specifically, conditions of washing once, more preferably 2-3 times, at the salt concentration and temperature corresponding to those in the washing conditions of general Southern hybridization (60° C., 1×SSC, 0.1% SDS, preferably, 0.1×SSC, 0.1% SDS, more preferably, 68° C., 0.1×SSC, 0.1% SDS) and the like.

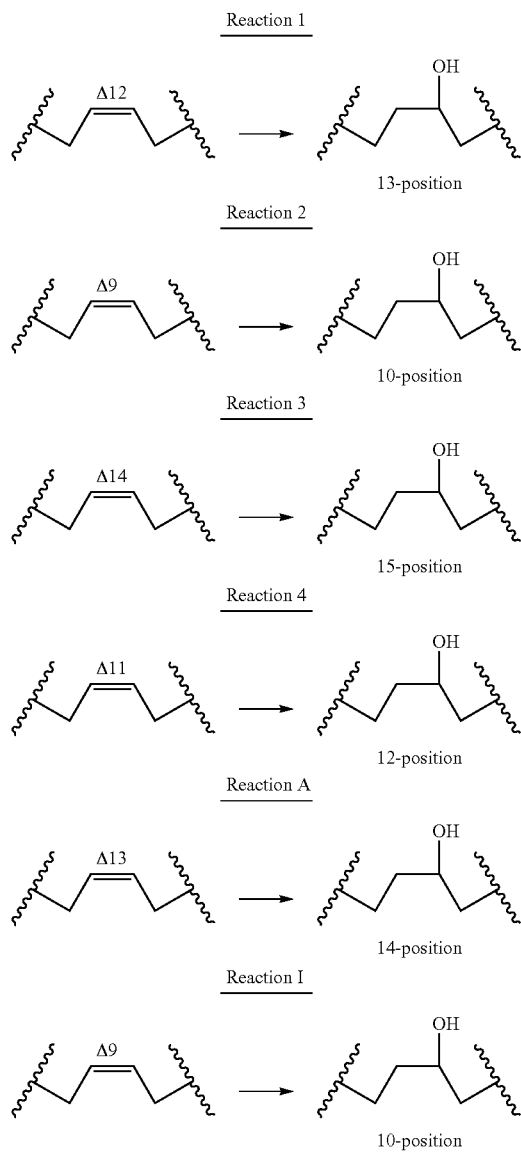

Regarding the above-mentioned (b) or (c), the enzyme activity that the enzyme protein consisting of the amino acid sequence shown in SEQ ID NO: 2 has is not particularly limited as long as it has at least one, preferably all, of (1) an enzyme activity capable of converting an unsaturated fatty acid having 18 carbon atoms and a cis double bond at the 12-position (hereinafter sometimes to be abbreviated as "cis-12 unsaturated fatty acid") utilized as a substrate to a hydroxylated fatty acid having 18 carbon atoms and a hydroxyl group at the 13-position (13-hydroxy fatty acid) (reaction 1), (2) an enzyme activity capable of converting an unsaturated fatty acid having 16 carbon atoms and a cis double bond at the 9-position (hereinafter sometimes to be abbreviated as "cis-9 unsaturated fatty acid")) utilized as a substrate to a hydroxylated fatty acid having 16 carbon atoms and a hydroxyl group at the 10-position (10-hydroxy fatty acid) (reaction 2), (3) an enzyme activity capable of converting an unsaturated fatty acid having 20 carbon atoms and a cis double bond at the 14-position (hereinafter sometimes to be abbreviated as "cis-14 unsaturated fatty acid")) utilized as a substrate to a hydroxylated fatty acid having 20 carbon atoms and a hydroxyl group at the 15-position (15-hydroxy fatty acid) (reaction 3), (4) an enzyme activity capable of converting an unsaturated fatty acid having 20 carbon atoms and a cis double bond at the 11-position (hereinafter sometimes to be abbreviated as "cis-11 unsaturated fatty acid")) utilized as a substrate to a hydroxylated fatty acid having 20 carbon atoms and a hydroxyl group at the 12-position (12-hydroxy fatty acid) (reaction 4), an enzyme activity capable of converting cis-4,cis-7,cis-10,cis-13,cis-16,cis-19-docosahexaenoic acid (DHA) to 14-hydroxy-cis-4,cis-7,cis-10,cis-16,cis-19-docosapentaenoic acid (reaction A), and an enzyme activity capable of converting cis-9-tetradecenoic acid (myristoleic acid) to 10-hydroxy-tetradecanoic acid (reaction I).

The above-mentioned "cis-12 unsaturated fatty acid", "cis-9 unsaturated fatty acid", "cis-14 unsaturated fatty acid", and "cis-11 unsaturated fatty acid" are not particularly limited as long as they are an unsaturated fatty acid having 18 carbon atoms and a cis double bond at the 12-position, an unsaturated fatty acid having 16 carbon atoms and a cis double bond at the 9-position, an unsaturated fatty acid having 20 carbon atoms and a cis double bond at the 14-position, an unsaturated fatty acid having 20 carbon atoms and a cis double bond at the 11-position, respectively and, for example, monovalent unsaturated fatty acid, divalent unsaturated fatty acid, trivalent unsaturated fatty acid, tetravalent unsaturated fatty acid, pentavalent unsaturated fatty acid and the like can be mentioned. In the-present specification, the "fatty acid" encompasses not only free acids but also ester form, salt with basic compound and the like. The "DHA" and "myristoleic acid" also encompass not only free acids but also ester form, salt with basic compound and the like.

The above-mentioned FA-HY can be isolated from, for example, the fungus, culture medium of *Lactobacillus acidophilus* by a protein separation and purification technique known per se. Alternatively, FA-HY may be used as the fungus of *Lactobacillus acidophilus* containing FA-HY or fungal debris thereof. The fungus of *Lactobacillus acidophilus* containing FA-HY is not particularly limited as long as it contains the above-mentioned FA-HY and, for example, NITE BP-01788 deposited on Jan. 17, 2014 at the NITE Patent Microorganisms Depositary (NPMD) and the like can be mentioned. Alternatively, FA-HY can also be produced as a recombinant protein by isolating a gene encoding FA-HY, subcloning same into a suitable vector, introducing same into a suitable host such as *Escherichia coli* and the like and culturing same. FA-HY may be a purified one or a crudely purified one. Alternatively, hydratase may be expressed in fungus such as *Escherichia coli* and the like and the fungus itself may be used or culture medium thereof may be used. Furthermore, the enzyme may be of a free form, or immobilized by various carriers.

As a vector containing a nucleic acid encoding the above-mentioned FA-HY, one suitable for a host cell to be introduced with the vector may be appropriately selected according to the object (e.g., protein expression) and can be used. In the case of an expression vector, it contains the nucleic acid of the present invention, which is operably linked to an appropriate promoter, and preferably contains a transcription termination signal, i.e., terminator region, at the downstream of the nucleic acid of the present invention. Furthermore, it can also contain a selection marker gene for selection of a transformant (drug resistance gene, gene that complements auxotrophic mutation etc.). Also, it may contain a sequence encoding a tag sequence useful for separation and purification of the expressed protein and the like. In addition, the vector may be incorporated into the genome of a target host cell. The vector of the present invention can be introduced into a target host cell by a transformation method known per se such as a competent cell method, a protoplast method, a calcium phosphate coprecipitation method and the like.

In the present specification, the "host cell" may be any cell as long as it can express a vector containing a nucleic acid encoding the above-mentioned FA-HY, and bacterium, yeast, fungi, higher eukaryotic cell and the like can be mentioned. Examples of the bacterium include gram-positive bacteria such as *bacillus, Streptomyces* and the like and gram negative bacteria such as *Escherichia coli* and the like. A recombinant cell introduced with a vector containing a nucleic acid encoding FA-HY can be cultivated by a method known per se which is suitable for the host cell.

"Purification" of the above-mentioned FA-HY can be performed by a method known per se, for example, fungi collected by centrifugation and the like are ruptured by ultrasonication or glass beads and the like, solid such as cell debris is removed by centrifugation and the like, and the like to give a crude enzyme solution, which is subjected to a salting out method using ammonium sulfate, sodium sulfate and the like, chromatographys such as ion exchange chromatography, gel filtration chromatography, affinity chromatography and the like, gel electrophoresis and the like.

The above-mentioned FA-HY has, as mentioned above, an enzyme activity capable of converting cis-12 unsaturated fatty acid, cis-9 unsaturated fatty acid, cis-14 unsaturated fatty acid, cis-11 unsaturated fatty acid, DHA, myristoleic acid utilized as substrates to 13-hydroxy fatty acid, 10-hydroxy fatty acid, 15-hydroxy fatty acid, 12-hydroxy fatty acid, 14-hydroxy-cis-4,cis-7,cis-10,cis-16,cis-19-docosapentaenoic acid, 10-hydroxy-tetradecanoic acid, respectively. Therefore, [1] a method of producing 13-hydroxy fatty acid from cis-12 unsaturated fatty acid by a hydration reaction using the above-mentioned FA-HY (production method 1), [2] a method of producing 10-hydroxy fatty acid from cis-9 unsaturated fatty acid by a hydration reaction using the above-mentioned FA-HY (production method 2), [3] a method of producing 15-hydroxy fatty acid from cis-14 unsaturated fatty acid by a hydration reaction using the above-mentioned FA-HY (production method 3), [4] a method of producing 12-hydroxy fatty acid from cis-11 unsaturated fatty acid by a hydration reaction using the above-mentioned FA-HY (production method 4), [A] a method of producing 14-hydroxy-cis-4,cis-7,cis-10,cis-16,cis-19-docosapentaenoic acid from DHA by a hydration reaction using the above-mentioned FA-HY (production method A), and [I] a method of producing 10-hydroxy-tetradecanoic acid from myristoleic acid by a hydration reaction using the FA-HY of the present invention (production method I) are provided.

Examples of the "cis-12 unsaturated fatty acid" in the above-mentioned production method 1 include cis-9,cis-12-octadecadienoic acid (linoleic acid), cis-6,cis-9,cis-12-octadecatrienoic acid (γ-linolenic acid), cis-9,cis-12,cis-15-octadecatrienoic acid (α-linolenic acid), cis-6,cis-9,cis-12,cis-15-octadecatetraenoic acid (stearidonic acid), as well as 10-hydroxy-cis-12-octadecenoic acid, 10-hydroxy-cis-6,cis-12-octadecadienoic acid, 10-hydroxy-cis-12,cis-15-octadecadienoic acid, 10-hydroxy-cis-6,cis-12,cis-15-octadecatrienoic acid, 10-oxo-cis-12-octadecenoic acid, 10-oxo-cis-6,cis-12-octadecadienoic acid, 10-oxo-cis-12,cis-15-octadecadienoic acid, 10-oxo-cis-6,cis-12,cis-15-octadecatrienoic acid, cis-5,cis-9,cis-12-octadecatrienoic acid (pinolenic acid), trans-5,cis-9,cis-12-octadecatrienoic acid (columbinic acid), which are now producible by WO 2013/168310, and the like. These substrates may be obtained by a method other than WO 2013/168310.

Examples of the "13-hydroxy fatty acid" produced by the above-mentioned production method 1 include 13-hydroxy-cis-9-octadecenoic acid induced from cis-9,cis-12-octadecadienoic acid (linoleic acid), 13-hydroxy-cis-6,cis-9-octadecadienoic acid induced from cis-6,cis-9,cis-12-octadecatrienoic acid (γ-linolenic acid), 13-hydroxy-cis-9,cis-15-octadecadienoic acid induced from cis-9,cis-12,cis-15-octadecatrienoic acid (α-linolenic acid), 13-hydroxy-cis-6,cis-9,cis-15-octadecatrienoic acid induced from cis-6,cis-9,cis-12,cis-15-octadecatetraenoic acid (stearidonic acid), 10,13-dihydroxy-octadecanoic acid induced from 10-hydroxy-cis-12-octadecenoic acid, 10,13-dihydroxy-cis-6-octadecenoic acid induced from 10-hydroxy-cis-6,cis-12-octadecadienoic acid, 10,13-dihydroxy-cis-15-octadecenoic acid induced from 10-hydroxy-cis-12,cis-15-octadecadienoic acid, 10,13-dihydroxy-cis-6,cis-15-octadecadienoic acid induced from 10-hydroxy-cis-6,cis-12,cis-15-octadecatrienoic acid, 10-oxo-13-hydroxy-octadecanoic acid induced from 10-oxo-cis-12-octadecenoic acid, 10-oxo-13-hydroxy-cis-6-octadecenoic acid induced from 10-oxo-cis-6,cis-12-octadecadienoic acid, 10-oxo-13-hydroxy-cis-15-octadecenoic acid induced from 10-oxo-cis-12,cis-15-octadecadienoic acid, 10-oxo-13-hydroxy-cis-6,cis-15-octadecadienoic acid induced from 10-oxo-cis-6,cis-12,cis-15-octadecatrienoic acid, 13-hydroxy-cis-5,cis-9-octadecadienoic acid induced from cis-5,cis-9,cis-12-octadecatrienoic acid (pinolenic acid), 13-hydroxy-trans-5,cis-9-octadecadienoic acid induced from trans-5,cis-9,cis-12-octadecatrienoic acid (columbinic acid) and the like.

Examples of the "cis-9 unsaturated fatty acid" in the above-mentioned production method 2 include cis-9-hexadecenoic acid (pulmitoleic acid) and the like.

Examples of the "10-hydroxy fatty acid" produced by the above-mentioned production method 2 include 10-hydroxy-hexadecanoic acid induced from cis-9-hexadecenoic acid (pulmitoleic acid) and the like.

Examples of the "cis-14 unsaturated fatty acid" in the above-mentioned production method 3 include cis-11,cis-14-eicosadienoic acid, cis-11,cis-14,cis-17-eicosatrienoic acid, cis-8,cis-11,cis-14-eicosatrienoic acid (dihomo-γ-linolenic acid), cis-5,cis-8,cis-11,cis-14-eicosatetraenoic acid (arachidonic acid), cis-8,cis-11,cis-14,cis-17-eicosatetraenoic acid, cis-5,cis-11,cis-14-eicosatrienoic acid (sciadonic acid), cis-5,cis-11,cis-14,cis-17-eicosatetraenoic acid (juniperonic acid) and the like.

Examples of the "15-hydroxy fatty acid" produced by production method 3 of the present invention include 15-hydroxy-cis-11-eicosenoic acid induced from cis-11,cis-14-eicosadienoic acid, 15-hydroxy-cis-11,cis-17-eicosadienoic acid induced from cis-11,cis-14,cis-17-eicosatrienoic acid, 15-hydroxy-cis-8,cis-11-eicosadienoic acid induced from cis-8,cis-11,cis-14-eicosatrienoic acid (dihomo-γ-linolenic acid), 15-hydroxy-cis-5,cis-8,cis-11-eicosatrienoic acid induced from cis-5,cis-8,cis-11,cis-14-eicosatetraenoic acid (arachidonic acid), 15-hydroxy-cis-8,cis-11,cis-17-eicosatrienoic acid induced from cis-8,cis-11,cis-14,cis-17-eicosatetraenoic acid, 15-hydroxy-cis-5,cis-11-eicosadienoic acid induced from cis-5,cis-11,cis-14-eicosatrienoic acid (sciadonic acid), 15-hydroxy-cis-5,cis-11,cis-17-eicosatrienoic acid induced from cis-5,cis-11,cis-14,cis-17-eicosatetraenoic acid (juniperonic acid) and the like.

Examples of the "cis-11 unsaturated fatty acid" in production method 4 of the present invention include cis-11,cis-14-eicosadienoic acid, cis-11,cis-14,cis-17-eicosatrienoic acid, cis-8,cis-11,cis-14-eicosatrienoic acid (dihomo-γ-linolenic acid), cis-5,cis-8,cis-11-eicosatrienoic acid (mead acid), cis-8,cis-11,cis-14,cis-17-eicosatetraenoic acid, cis-5,cis-8,cis-11,cis-14-eicosatetraenoic acid (arachidonic acid) and the like.

Examples of the "12-hydroxy fatty acid" produced by production method 4 of the present invention include 12-hydroxy-cis-14-eicosenoic acid induced from cis-11,cis-14-eicosadienoic acid, 12-hydroxy-cis-14,cis-17-eicosadienoic acid induced from cis-11,cis-14,cis-17-eicosatrienoic acid, 12-hydroxy-cis-8,cis-14-eicosadienoic acid induced from cis-8,cis-11,cis-14-eicosatrienoic acid (dihomo-γ-linolenic acid), 12-hydroxy-cis-5,cis-8-eicosadienoic acid induced from cis-5,cis-8,cis-11-eicosatrienoic acid (mead acid), 12-hydroxy-cis-8,cis-14,cis-17-eicosatrienoic acid induced from cis-8,cis-11,cis-14,cis-17-eicosatetraenoic acid, 12-hydroxy-cis-5,cis-8,cis-14-eicosatrienoic acid induced from cis-5,cis-8,cis-11,cis-14-eicosatetraenoic acid (arachidonic acid) and the like.

The hydration reaction may be performed in a suitable buffer (e.g., phosphate buffer, tris buffer, borate buffer etc.) by mixing unsaturated fatty acid, which is a substrate, and the above-mentioned FA-HY at suitable concentrations and incubating the mixture. The substrate concentration is, for example, 1-1000 g/L, preferably 10-500 g/L, more preferably 20-250 g/L. The amount of the aforementioned FA-HY to be added is, for example, 0.001-10 mg/mL, preferably 0.1-5 mg/mL, more preferably 0.2-2 mg/mL.

A "cofactor" may be used for a hydration reaction (reaction 1-4, reaction A or reaction I) and, for example, FAD and the like can be used. The concentration of addition may be any as long as the hydration reaction proceeds efficiently. It is preferably 0.001-20 mM, more preferably 0.01-10 mM.

Furthermore, an "activator" may be used for the hydration reaction and, for example, 1 or 2 compounds selected from the group consisting of NADH and NADPH can be mentioned. The concentration of addition thereof may be any as long as the hydration reaction proceeds efficiently. It is preferably 0.1-20 mM, more preferably 1-10 mM.

The hydration reaction is desirably performed at a preferable temperature and in a preferable pH range for the above-mentioned FA-HY. For example, the reaction temperature is 5-50° C., preferably 20-45° C. The pH of the reaction mixture is, for example, pH 4-10, preferably pH 5-9. The reaction time is not particularly limited and it is, for example, 10 min-72 hr, preferably 30 min-36 hr.

In one preferable embodiment of the present invention, the above-mentioned FA-HY is provided to the reaction system in the form of recombinant cells (e.g., *Escherichia coli, Bacillus subtilis*, yeast, insect cell, animal cell etc.) introduced with an expression vector containing a nucleic acid encoding same. In this case, the hydration reaction can also be performed by cultivating the cells in a liquid medium suitable for the culture of the cells and added with cofactor and a substrate and, where necessary, an activator.

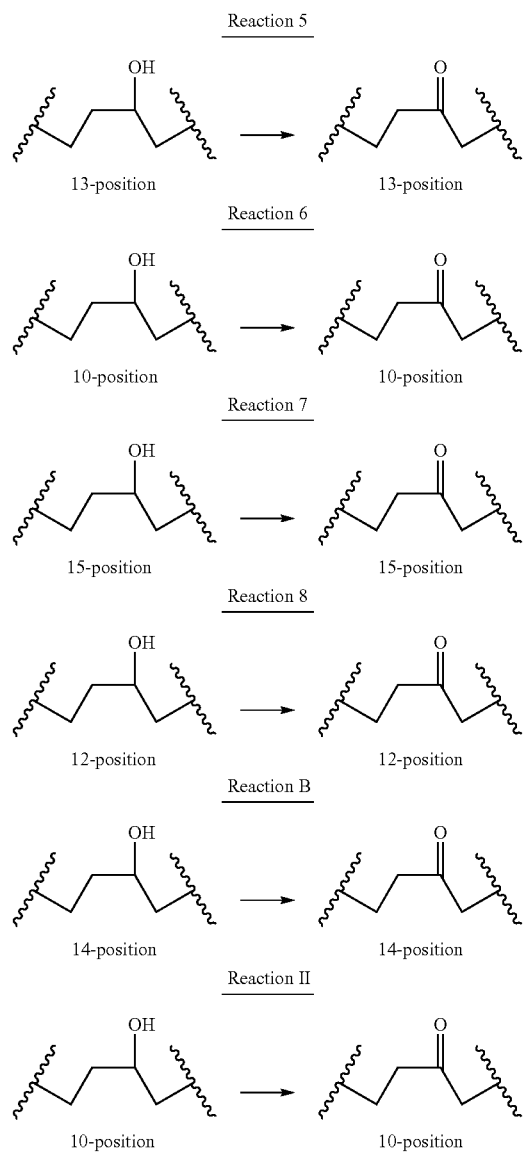

Furthermore, by a dehydrogenation reaction or chemical oxidation using chrome acid, an oxo fatty acid having 18 carbon atoms and a carbonyl group at the 13-position (hereinafter sometimes to be abbreviated as "13-oxo fatty acid") is produced from 13-hydroxy fatty acid obtained in the above-mentioned production methods 1-4, production method A, production method I (reaction 5), an oxo fatty acid having 16 carbon atoms and a carbonyl group at the 10-position (hereinafter sometimes to be abbreviated as "10-oxo fatty acid") is produced from 10-hydroxy fatty acid (reaction 6), an oxo fatty acid having 20 carbon atoms and a carbonyl group at the 15-position (hereinafter sometimes to be abbreviated as "15-oxo fatty acid") is produced from 15-hydroxy fatty acid (reaction 7), an oxo fatty acid having 20 carbon atoms and a carbonyl group at the 12-position (hereinafter sometimes to be abbreviated as "12-oxo fatty acid") is produced from 12-hydroxy fatty acid (reaction 8), 14-oxo-cis-4,cis-7,cis-10,cis-16,cis-19-docosapentaenoic acid is produced from 14-hydroxy-cis-4,cis-7,cis-10,cis-16,cis-19-docosapentaenoic acid (reaction B), and 10-oxo-tetradecanoic acid is produced from 10-hydroxy-tetradecanoic acid (reaction II).

Therefore, [5] a method of producing 13-oxo fatty acid, comprising subjecting cis-12 unsaturated fatty acid to a hydration reaction using the above-mentioned FA-HY to induce 13-hydroxy fatty acid, and subjecting the 13-hydroxy fatty acid to a dehydrogenation reaction or chemical oxidation (production method 5), [6] a method of producing 10-oxo fatty acid, comprising subjecting cis-9 unsaturated fatty acid to a hydration reaction using the above-mentioned FA-HY to induce 10-hydroxy fatty acid, and subjecting the 10-hydroxy fatty acid to a dehydrogenation reaction or chemical oxidation (production method 6), [7] a method of producing 15-oxo fatty acid, comprising subjecting cis-14 unsaturated fatty acid to a hydration reaction using the above-mentioned FA-HY to induce 15-hydroxy fatty acid, and subjecting the 15-hydroxy fatty acid to a dehydrogenation reaction or chemical oxidation (production method 7), [8] a method of producing 12-oxo fatty acid, comprising subjecting cis-11 unsaturated fatty acid to a hydration reaction using the above-mentioned FA-HY to induce 12-hydroxy fatty acid, and subjecting the 12-hydroxy fatty acid to a dehydrogenation reaction or chemical oxidation (production method 8), [B] a method of producing 14-oxo-cis-4,cis-7,cis-10,cis-16,cis-19-docosapentaenoic acid, comprising subjecting DHA to a hydration reaction using the FA-HY of the present invention to induce 14-hydroxy-cis-4,cis-7, cis-10,cis-16,cis-19-docosapentaenoic acid, and subjecting the 14-hydroxy-cis-4,cis-7,cis-10,cis-16,cis-19-docosapentaenoic acid to a dehydrogenation reaction or chemical oxidation (production method B), and [II] a method of producing 10-oxo-tetradecanoic acid, comprising subjecting myristoleic acid to a hydration reaction using the FA-HY of the present invention to induce 10-hydroxy-tetradecanoic acid, and subjecting the 10-hydroxy-tetradecanoic acid to a dehydrogenation reaction or chemical oxidation (production method II) are provided.

The "cis-12 unsaturated fatty acid", "cis-9 unsaturated fatty acid", "cis-14 unsaturated fatty acid", "cis-11 unsaturated fatty acid" in the above-mentioned production methods 5-8 are the same as the substrates in the above-mentioned production methods 1-4.

Examples of the "13-oxo fatty acid" produced by the above-mentioned production method 5 include 13-oxo-cis-9-octadecenoic acid induced from cis-9,cis-12-octadecadienoic acid (linoleic acid), 13-oxo-cis-6,cis-9-octadecadienoic acid induced from cis-6,cis-9,cis-12-octadecatrienoic acid (γ-linolenic acid), 13-oxo-cis-9,cis-15-octadecadienoic acid induced from cis-9,cis-12,cis-15-octadecatrienoic acid (α-linolenic acid), 13-oxo-cis-6,cis-9,cis-15-octadecatrienoic acid induced from cis-6,cis-9,cis-12,cis-15-octadecatetraenoic acid (stearidonic acid), 10,13-dioxo-octadecanoic acid induced from 10-hydroxy-cis-12-octadecenoic acid or 10-oxo-cis-12-octadecenoic acid, 10,13-dioxo-cis-6-octadecenoic acid induced from 10-hydroxy-cis-6,cis-12-octadecadienoic acid or 10-oxo-cis-6,cis-12-octadecadienoic acid, 10,13-dioxo-cis-15-octadecenoic acid induced from 10-hydroxy-cis-12,cis-15-octadecadienoic acid or 10-oxo-cis-12,cis-15-octadecadienoic acid, 10,13-dioxo-cis-6,cis-15-octadecadienoic acid induced from 10-hydroxy-cis-6,cis-12,cis-15-octadecatrienoic acid or 10-oxo-cis-6,cis-12,cis-15-octadecatrienoic acid, 13-oxo-cis-5,cis-9-octadecadienoic acid induced from cis-5,cis-9,cis-12-octadecatrienoic acid (pinolenic acid), 13-oxo-trans-5,cis-9-octadecadienoic acid induced from trans-5,cis-9,cis-12-octadecatrienoic acid (columbinic acid) and the like.

Examples of the "10-oxo fatty acid" produced by the above-mentioned production method 6 include 10-oxo-hexadecanoic acid induced from cis-9-hexadecenoic acid (pulmitoleic acid) and the like.

Examples of the "15-oxo fatty acid" produced by the above-mentioned production method 7 include 15-oxo-cis-11-eicosenoic acid induced from cis-11,cis-14-eicosadienoic acid, 15-oxo-cis-11,cis-17-eicosadienoic acid induced from cis-11,cis-14,cis-17-eicosatrienoic acid, 15-oxo-cis-8,cis-11-eicosadienoic acid induced from cis-8,cis-11,cis-14-eicosatrienoic acid (dihomo-γ-linolenic acid), 15-oxo-cis-5,cis-8,cis-11-eicosatrienoic acid induced from cis-5,cis-8,cis-11,cis-14-eicosatetraenoic acid (arachidonic acid), 15-oxo-cis-8,cis-11,cis-17-eicosatrienoic acid induced from cis-8,cis-11,cis-14,cis-17-eicosatetraenoic acid, 15-oxo-cis-5,cis-11-eicosadienoic acid induced from cis-5,cis-11,cis-14-eicosatrienoic acid (sciadonic acid), 15-oxo-cis-5,cis-11,cis-17-eicosatrienoic acid induced from cis-5,cis-11,cis-14,cis-17-eicosatetraenoic acid (juniperonic acid) and the like.

Examples of the "12-oxo fatty acid" produced by the above-mentioned production method 8 include 12-oxo-cis-14-eicosenoic acid induced from cis-11,cis-14-eicosadienoic acid, 12-oxo-cis-14,cis-17-eicosadienoic acid induced from cis-11,cis-14,cis-17-eicosatrienoic acid, 12-oxo-cis-8,cis-14-eicosadienoic acid induced from cis-8,cis-11,cis-14-eicosatrienoic acid (dihomo-γ-linolenic acid), 12-oxo-cis-5,cis-8-eicosadienoic acid induced from cis-5,cis-8,cis-11-eicosatrienoic acid (mead acid), 12-oxo-cis-8,cis-14,cis-17-eicosatrienoic acid induced from cis-8,cis-11,cis-14,cis-17-eicosatetraenoic acid, 12-oxo-cis-5,cis-8,cis-14-eicosatrienoic acid induced from cis-5,cis-8,cis-11,cis-14-eicosatetraenoic acid (arachidonic acid) and the like.

The dehydrogenase to be used in the above-mentioned production methods 5-8, production method B or production method II is not particularly limited as long as it is an enzyme capable of converting 13-hydroxy fatty acid, 10-hydroxy fatty acid, 15-hydroxy fatty acid, 12-hydroxy fatty acid, 14-hydroxy-cis-4,cis-7,cis-10,cis-16,cis-19-docosapentaenoic acid, 10-hydroxy-tetradecanoic acid utilized as substrates to 13-oxo fatty acid, 10-oxo fatty acid, 15-oxo fatty acid, 12-oxo fatty acid, 14-oxo-cis-4,cis-7,cis-10,cis-16,cis-19-docosapentaenoic acid, 10-oxo-tetradecanoic acid, respectively and, for example, *lactobacillus*-derived hydroxylated fatty acid-dehydrogenase (CLA-DH) is preferable. More preferred is *Lactobacillus plantarum*-derived CLA-DH, and particularly preferred is *L. plantarum* FERM BP-10549 strain-derived CLA-DH. CLA-DH can be obtained by the method described in JP-A-2007-259712, the method described in WO 2013/168310. Dehydrogenase may be a purified one or a crudely purified one. Alternatively, dehydrogenase may be expressed in fungus such as *Escherichia coli* and the like and the fungus itself may be used or culture medium thereof may be used. Furthermore, the enzyme may be of a free form, or immobilized by various carriers.

The dehydrogenation reaction is performed in a suitable buffer (e.g., phosphate buffer, tris buffer, borate buffer etc.)

by mixing 13-hydroxy fatty acid, 10-hydroxy fatty acid, 15-hydroxy fatty acid, 12-hydroxy fatty acid, 14-hydroxy-cis-4,cis-7,cis-10,cis-16,cis-19-docosapentaenoic acid, 10-hydroxy-tetradecanoic acid as substrates and dehydrogenase at suitable concentrations and incubating the mixture. The substrate concentration is, for example, 0.01-100 g/L, preferably 0.05-50 g/L, more preferably 0.1-5 g/L. The amount of dehydrogenase to be added is, for example, 0.001-10 mg/mL, preferably 0.005-1 mg/mL, more preferably 0.05-0.2 mg/mL.

A "cofactor" may be used for the dehydrogenation reaction and, for example, $NAD^+$, $NADP^+$ and the like can be used. The concentration of addition thereof may be any as long as the hydration reaction proceeds efficiently. It is preferably 0.001-20 mM, more preferably 0.01-10 mM.

The dehydrogenation reaction is desirably performed within the ranges of preferable temperature and preferable pH of dehydrogenase. For example, the reaction temperature is 5-50° C., preferably 20-45° C. The pH of the reaction mixture is, for example, pH 4-10, preferably pH 5-9. The reaction time is not particularly limited and it is, for example, 10 min-72 hr, preferably 30 min-36 hr.

In one embodiment of the present invention, dehydrogenase is subjected to the reaction system in the form of recombinant cells (e.g., *Escherichia coli*, *Bacillus subtilis*, yeast, insect cell, animal cell etc.) introduced with an expression vector containing a nucleic acid encoding same. In this case, the oxidation reaction can also be performed by cultivating the cells in a liquid medium suitable for the culture of the cells and added with a substrate and, where necessary, a cofactor and an activator.

In addition, by replacing the dehydrogenation reaction with a chemical oxidation using chromic acid, an oxo fatty acid similar to that by enzyme reaction can be chemically obtained.

As the chemical oxidation, methods known per se, for example, chromic acid oxidation, preferably Jones oxidation and the like can be mentioned. As the chromic acid, salts or complexes of the compound such as anhydrous chromic acid $CrO_3$, chromic acid $H_2CrO_4$ and dichromic acid $H_2Cr_2O_7$ can be used. To be specific, sulfuric acid (2.3 ml) and water (7.7 ml) are added to anhydrous chromic acid (2.67 g), and acetone (90 ml) is added to the mixture to give a chromic acid solution. 2 g of hydroxylated fatty acid and 40 ml of acetone are added in an Erlenmeyer flask, and the above-mentioned chromic acid solution is added by one drop while stirring in a stirrer on ice. When the solution turns from blue to tea green, dropwise addition of the chromic acid solution is stopped, and the reaction is discontinued with isopropyl alcohol. The precipitated sediment is filtered through filter paper, placed in a separating funnel, diethyl ether (150 ml) and Milli-Q water (300 ml) are added, the mixture is shaken well, and the diethyl ether layer is washed several times with Milli-Q water. To the diethyl ether layer after washing is added an appropriate amount of sodium sulfate (anhydrous), the mixture is stirred and the residual water is removed. The anhydrous sodium sulfate added is filtered off through filter paper, the obtained diethyl ether layer is concentrated by a rotary evaporator, and the reaction product (oxo fatty acid) and unreacted substrate are extracted.

An extract obtained by an oxidation reaction with anhydrous chromic acid (mixture containing substrate and resultant product (oxo fatty acid)) is subjected to moderate-pressure chromatography, a solution that comes out from the column is recovered in fractions. The recovered each fraction is analyzed by LC/MS and gas chromatography, fractions containing oxo fatty acid alone are collected and concentrated by a rotary evaporator. A part of the obtained final resultant product is ethylesterified, the purity of oxo fatty acid is evaluated by gas chromatography, and oxo fatty acid having a purity of not less than 98% can be obtained.

The metabolism improving agent containing the rare fatty acid of the present invention can also be applied to the improvement of lifestyle-related diseases. The "lifestyle-related disease" is a disease group for which life habits such as eating habit, exercise habit, rest, smoking, drinking and the like are involved in the onset and progression thereof, and includes pathologies such as adult obesity, child obesity, nutrition ataxia, anorexia, gastric cancer, large intestine cancer, gout, hypertension, arteriosclerosis, nephrolithiasis, myocardial infarction, angina pectoris, gastric ulcer, kidney disease, osteoporosis, periodontitis, alcoholic hepatitis, cirrhosis, liver cancer, lung cancer, bronchitis, emphysema, periodontal disease, cerebral apoplexy, cerebral infarction, aneurysm, overwork death, insomnia and the like.

Moreover, the metabolism improving agent of the present invention can also be used for the prophylaxis or improvement of diabetes (type 1 diabetes, type 2 diabetes, pregnancy diabetes etc.), diabetic complications (arteriosclerotic diseases, diabetic retinopathy, diabetic nephropathy, diabetic neuropathy etc.), lipid metabolism abnormality, hyperlipidemia, hypercholesterolemia, hypertriglyceridemia, insulin resistance, and fatty liver.

Alternatively, the metabolism improving agent of the present invention can be used for the prophylaxis or treatment of at least one kind selected from the group consisting of obesity, diabetes, lipid metabolism abnormality, hyperlipidemia, hypercholesterolemia, hypertriglyceridemia, insulin resistance and fatty liver, by administration to human, or an animal other than human (e.g., dog, cat, mouse, rat, hamster, guinea pig, rabbit, swine, bovine, chicken, parakeet, hill myna, goat, horse, sheep, monkey etc.).

The rare fatty acid of the present invention can also be used as a PPAR activity promoter. PPAR includes at least 3 kinds of subtypes PPARα, PPARδ (same as β), and PPARγ. As shown in the below-mentioned Examples, the rare fatty acid of the present invention has an agonist activity on PPARα, PPARγ. Therefore, when at least one kind of PPAR (preferably PPARα or PPARγ) from among these PPARs is confirmed for the presence or absence of a ligand (agonist, antagonist) activity and an agonist activity is shown, it can be used as a promoter of PPAR activity for the improvement of metabolism. The metabolism improving agent (or PPAR activity promoter) containing the rare fatty acid of the present invention can be used as, for example, a pharmaceutical product, a food, a feed, a cosmetic and the like, or by adding the agent to them.

The dosage form of the pharmaceutical product includes dispersion, granule, pill, soft capsule, hard capsules, tablet, chewable tablet, quick-integrating tablet, syrup, liquid, suspension, suppository, ointment, cream, gel, adhesive, inhalant, injection and the like. A preparation thereof is prepared according to a conventional method. Since hydroxylated fatty acid and the like are poorly soluble in water, they are dissolved in a non-hydrophilic organic solvent such as plant-derived oil, animal-derived oil and the like or dispersed or emulsified in an aqueous solution together with an emulsifier, a dispersing agent, a surfactant and the like by a homogenizer (high-pressure homogenizer) and used.

Examples of the additives that can be used for formulating include animal and plant oils such as soybean oil, safflower oil, olive oil, germ oil, sunflower oil, beef fat, sardine oil and the like, polyalcohols such as polyethylene glycol, propylene glycol, glycerol, sorbitol and the like, surfactants such as sorbitan ester of fatty acid, sucrose ester of fatty acid, glycerin fatty acid ester, polyglycerol ester of fatty acid and the like, excipients such as purified water, lactose, starch, crystalline cellulose, D-mannitol, lecithin, gum arabic, sorbitol solution, carbohydrate solution and the like, sweetener, colorant, pH adjuster, flavor and the like. A liquid preparation may be dissolved or suspended in water or other suitable medium when in use. Also, tablet and granules may be coated by a well-known method.

For administration in the form of an injection, intravenous, intraperitoneal, intramuscular, subcutaneous, transdermal, intraarticular, intrasynovial, intrathecal, intraperiosteum, sublingual, oral administrations and the like are preferable, and intravenous administration or intraperitoneal administration is particularly preferable. The intravenous administration may be any of drip administration and bolus administration.

When the metabolism improving agent of the present invention is used as a food or a food additive, the form of the food is not particularly limited as long as it permits oral ingestion, such as solution, suspension, powder, solid formed article and the like. Specific examples include supplements (powder, granule, soft capsule, hard capsule, tablet, chewable tablet, quick-integrating tablet, syrup, liquid etc.), drinks (carbonic acid drinks, lactic acid drinks, sport drinks, fruit juice drinks, vegetable drinks, soymilk beverage, coffee drinks, tea drinks, powder drinks, concentrated drinks, nutrition drinks, alcohol drinks etc.), confectionery (gummy candy, jelly, gum, chocolate, cookie, candy, caramel, Japanese confectionery, snack etc.), instant food (instant noodles, retort food, can, microwavable foods, instant soup, miso soups, freeze-dried food etc.), oil, fats and oils food (mayonnaise, dressing, butter, cream, margarine etc.), wheat powder products (bread, pasta, noodle, cake mix, bread crumb etc.), seasoning (sauce, tomato processing seasoning, flavor seasoning, cooking mixture, soup etc.), processed meat products (meat ham, sausage etc.).

The above-mentioned foods can contain, where necessary, various nutrients, various vitamins (vitamin A, vitamin B1, vitamin B2, vitamin B6, vitamin C, vitamin D, vitamin E, vitamin K etc.), various minerals (magnesium, zinc, iron, sodium, potassium, selenium etc.), dietary fiber, dispersing agent, stabilizer such as emulsifier and the like, sweetener, flavor components (citric acid, malic acid etc.), flavor, royal jelly, propolis, Agaricus and the like.

When the metabolism improving agent of the present invention is used as a feed or a feed additive, the feed is, for example, pet food, stock raising or aquaculture feed additive and the like.

When the metabolism improving agent of the present invention is used as a cosmetic or a cosmetic additive, the cosmetic is, for example, cream, gel, skin milk, serum, toner, microemulsion essence, facial mask, foundation, lip rouge, eye shadow, shampoo, conditioner, bath additive and the like, and a flavor and the like may be mixed therewith.

Only one kind of hydroxylated fatty acid and oxo fatty acid and the like may be blended with the pharmaceutical product, food, feed, cosmetic and the like of the present invention or two or more kinds thereof may be used in combination.

The dose of the pharmaceutical product of the present invention or the ingestion amount of the food of the present invention can be appropriately determined according to the age and body weight of the patients or those who ingest same, symptom, administration time, dosage form, administration method, combination of medicaments and the like.

For example, when the pharmaceutical product of the present invention is orally administered, the total amount of the hydroxylated fatty acid and the like as an active ingredient is 0.02-100 mg/kg body weight, preferably 0.2-50 mg/kg body weight, per day for an adult, or 0.002 mg-50 mg/kg body weight, preferably 0.02-50 mg/kg body weight, by parenteral administration, which can be administered once a day or in several (2-5) portions per day. When it is ingested as a food, it can be added to a food such that the total ingestion amount of the hydroxylated fatty acid and the like as an active ingredient is 1-6000 mg, preferably 10-3000 mg, per day for an adult. The ingestion amount of the feed of the present invention and the amount of use of the cosmetic of the present invention can each appropriately determined according to the above-mentioned ingestion amount of the food and the above-mentioned dose of the pharmaceutical product.

The present invention is explained in more detail in the following by referring to Examples. The Examples are mere exemplifications of the present invention and do not limit the scope of the present invention in any manner.

EXAMPLE

The hydroxylated fatty acid and oxo fatty acid and the like, such as (1) 13-hydroxy-cis-9-octadecenoic acid (indicated as "13-OH LA"), (2) 13-oxo-cis-9-octadecenoic acid (indicated as "13-OXO LA"), (3) 10,13-dihydroxy-octadecanoic acid (indicated as "10,13-OH LA"), (4) 13-hydroxy-cis-9,cis-15-octadecadienoic acid (indicated as "13-OH ALA"), (5) 13-oxo-cis-9,cis-15-octadecadienoic acid (indicated as "13-OXO ALA"), (6) 10,13-dihydroxy-cis-15-octadecenoic acid (indicated as "10,13-OH ALA") (7) 13-hydroxy-cis-6,cis-9-octadecadienoic acid (indicated as "13-OH GLA"), (8) 13-oxo-cis-6,cis-9-octadecadienoic acid (indicated as "13-OXO GLA"), (9) 10,13-dihydroxy-cis-6-octadecenoic acid (indicated as "10,13-OH GLA"), (10) 15-hydroxy-cis-5,cis-8,cis-11-eicosatrienoic acid (indicated as "15-OH AA") and the like used in the present invention were prepared based on the above-mentioned methods. The structural formulas (1)-(10) and the fatty acids derived therefrom are shown in FIG. 1. GW7647 (PPARα agonist) and Troglitazone (PPARγ agonist) were purchased from Sigma-Aldrich, and other reagents were purchased from Wako Pure Chemical Industries, Ltd. or Nacalai Tesque and the like.

(Example 1) Measurement of PPARα, γ Ligand Activity

To evaluate the function of hydroxylated fatty acid and oxo fatty acid and the like, PPARα, γ-activating action was measured first. The measurement was performed in reference to Nobuyuki Takahashi et al., FEES Letters 514 (2002) p. 315-322, "Dual action of isoprenols from herbal medicines on both PPARgamma and PPARalpha in 3T3-L1 adipocytes and HepG2 hepatocytes.", the section of Materials and Methods "Reporter plasmids and luciferase assays". To be specific, PPARα,γ ligand activity was measured by a reporter assay that evaluates binding to a fusion protein of PPAR ligand binding region and GAL4 DNA binding region and target gene activation, based on the expression of luciferase. Specifically, a plasmid comprising a DNA encoding a fusion protein of PPARα,γ ligand binding region and GAL4 DNA binding region and a reporter plasmid wherein luciferase linked to GAL4 bound DNA sequence were introduced into CV-1 cell, a ligand described below was added to the cell, the cell was incubated and the luciferase activity was detected.

The concentration (10 μM and 30 μM) of the sample was adjusted with ethanol. Ethanol was used as a negative control, and PPARα,γ ligands GW7647 (10 nM) and troglitazone (5 μM) were used as a positive control. The results are shown in FIG. 2, FIG. 3.

Figure 3:
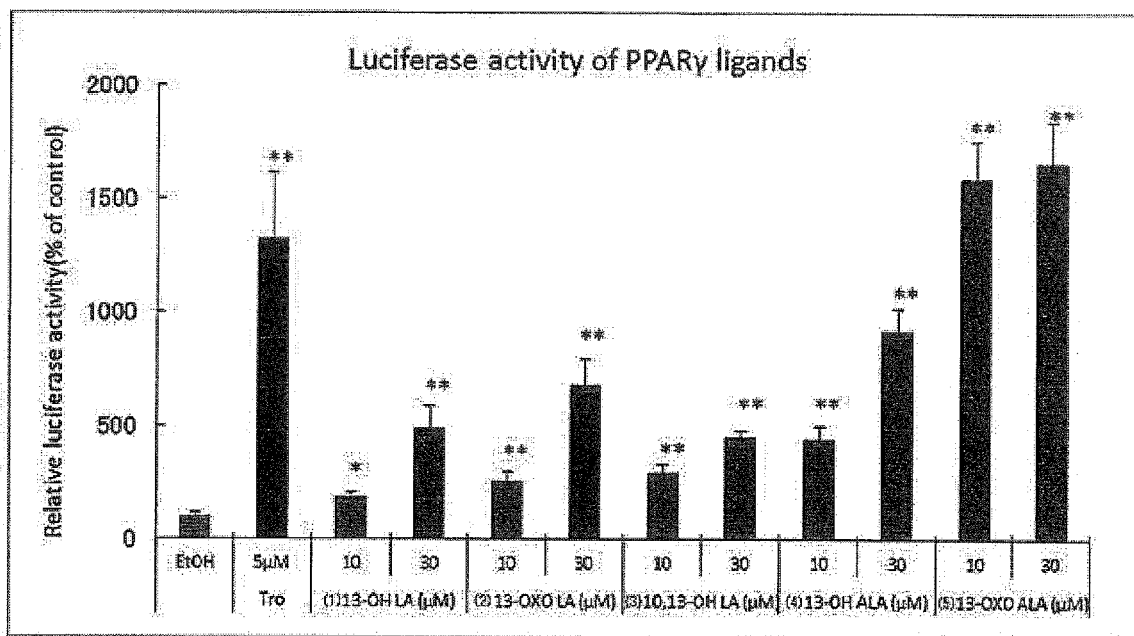
FIG. 3 shows the results of PPARγ agonist activity of hydroxylated fatty acid and oxo fatty acid, wherein EtOH shows negative control (ethanol addition), Tro shows positive control (PPARγ agonist addition), and the vertical axis shows relative luciferase activity.
Figure 3:
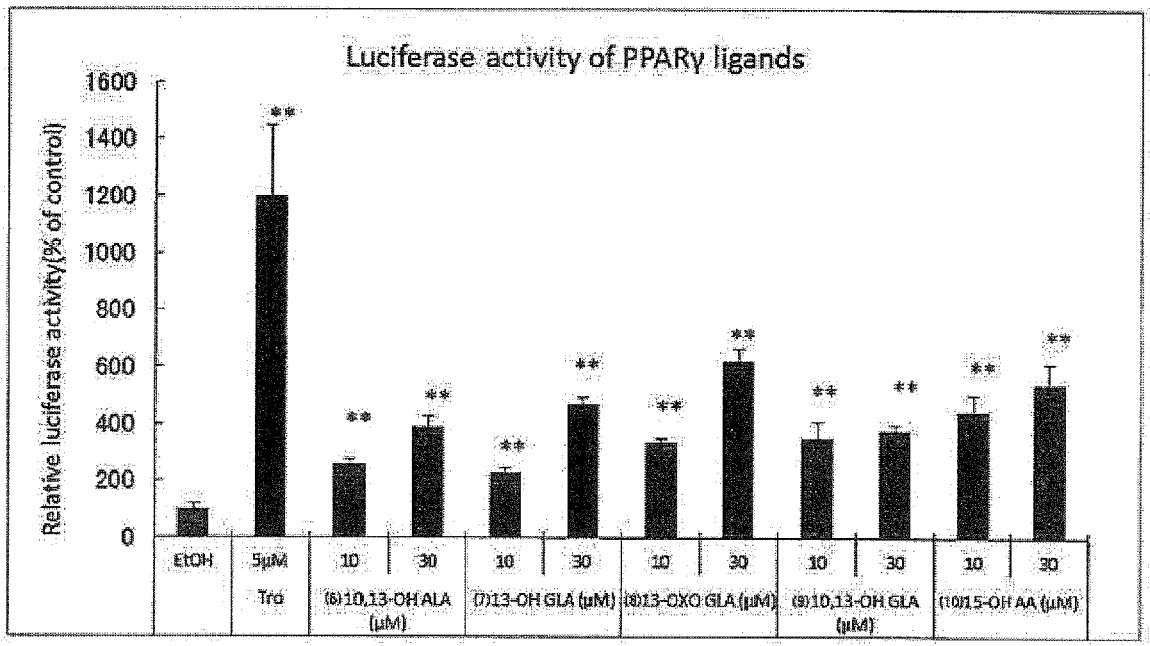

From FIGS. 2, 3, a PPARα and γ agonist activity was found in all fatty acids (1)-(10). In addition, (8) 13-OXO GLA showed a strong PPARα agonist activity, and (5) 13-OXO ALA showed a strong PPARγ agonist activity.

While the present invention has been described with emphasis on preferred embodiments, it is obvious to those skilled in the art that the preferred embodiments can be modified.

The contents disclosed in any publication cited herein, including patents and patent applications, are hereby incorporated in their entireties by reference, to the extent that they have been disclosed herein.

INDUSTRIAL APPLICABILITY

The present invention has clarified hydroxylated fatty acid and the like have a conventionally-unknown lipid and/or sugar and/or energy metabolism improving effect as a physiological function thereof. A lipid and/or sugar and/or energy metabolism improving agent containing the hydroxylated fatty acid and/or oxo fatty acid and the like is applicable to various fields such as pharmaceutical product, food, feed and the like, and the present invention is industrially extremely useful.

This application is based on a patent application No. 2014-011871 filed in Japan (filing date: Jan. 24, 2014), the contents of which are incorporated in full herein.

The invention claimed is:

1. A method for the treatment of hyperlipidemia, comprising administering to a patient having hyperlipidemia an effective amount of a fatty acid selected from the group consisting of
13-hydroxy-cis-9,cis-15-octadecadienoic acid, 10-oxo-13-hydroxy-cis-15-octadecenoic acid, 13-oxo-cis-6,cis-9-octadecadienoic acid, 13-oxo-cis-9,cis-15-octadecadienoic acid, and 10,13-dioxo-cis-15-octadecenoic acid.

2. The method according to claim 1, wherein an effective amount of 13-hydroxy-cis-9,cis-15-octadecadienoic acid is administered to the patient.

3. A method for promoting a PPAR activity, wherein the PPAR is PPARα or PPARγ, comprising administering to a patient having hyperlipidemia an effective amount of a fatty acid selected from the group consisting of
13-hydroxy-cis-9,cis-15-octadecadienoic acid, 10-oxo-13-hydroxy-cis-15-octadecenoic acid, 13-oxo-cis-6,cis-9-octadecadienoic acid, 13-oxo-cis-9,cis-15-octadecadienoic acid, and 10,13-dioxo-cis-15-octadecenoic acid.

4. The method according to claim 3, wherein an effective amount of 13-hydroxy-cis-9,cis-15-octadecadienoic acid, is administered to the patient.

5. The method according to claim 3, wherein an effective amount of 10-oxo-13-hydroxy-cis-15-octadecenoic acid is administered to the patient.

6. The method according to claim 3, wherein an effective amount of 13-oxo-cis-6,cis-9-octadecadienoic acid is administered to the patient.

7. The method according to claim 3, wherein an effective amount of 13-oxo-cis-9,cis-15-octadecadienoic acid is administered to the patient.

8. The method according to claim 3, wherein an effective amount of 10,13-dioxo-cis-15-octadecenoic acid is administered to the patient.

9. The method according to claim 1, wherein an effective amount of 10-oxo-13-hydroxy-cis-15-octadecenoic acid is administered to the patient.

10. The method according to claim 1, wherein an effective amount of 13-oxo-cis-6,cis-9-octadecadienoic acid is administered to the patient.

11. The method according to claim 1, wherein an effective amount of 13-oxo-cis-9,cis-15-octadecadienoic acid is administered to the patient.

12. The method according to claim 1, wherein an effective amount of 10,13-dioxo-cis-15-octadecenoic acid is administered to the patient.

* * * * *

SEQUENCE LISTING

```
<160> NUMBER OF SEQ ID NOS: 2

<210> SEQ ID NO 1
<211> LENGTH: 1773
<212> TYPE: DNA
<213> ORGANISM: Lactobacillus acidophilus
<220> FEATURE:
<221> NAME/KEY: CDS
<222> LOCATION: (1)..(1773)

<400> SEQUENCE: 1 atg cat tat agt agt ggt aat tat gaa gct ttt gta aac gca agt aaa      48
Met His Tyr Ser Ser Gly Asn Tyr Glu Ala Phe Val Asn Ala Ser Lys
1               5                   10                  15 cct aag gat gtc gat cag aag tcc gca tat ctt gtt ggt tca ggt ttg      96
Pro Lys Asp Val Asp Gln Lys Ser Ala Tyr Leu Val Gly Ser Gly Leu
            20                  25                  30 gca tcg ctt gct agt gct gta ttt tta att cgt gat ggt cac atg aag     144
Ala Ser Leu Ala Ser Ala Val Phe Leu Ile Arg Asp Gly His Met Lys
        35                  40                  45 ggt gat aga att cat atc ctt gaa gaa ttg agc ctt cca ggt ggt tca     192
Gly Asp Arg Ile His Ile Leu Glu Glu Leu Ser Leu Pro Gly Gly Ser
    50                  55                  60 atg gat ggg atc tat aat aag caa aaa gaa agc tac atc att cgt ggt     240
Met Asp Gly Ile Tyr Asn Lys Gln Lys Glu Ser Tyr Ile Ile Arg Gly
65                  70                  75                  80 ggt cgt gaa atg gaa gcc cat ttt gaa tgc ttg tgg gac ttg ttt aga     288
Gly Arg Glu Met Glu Ala His Phe Glu Cys Leu Trp Asp Leu Phe Arg
                85                  90                  95 tcg att cca tca gct gaa aat aaa gat gaa tcg gtc ctg gat gaa ttt     336
Ser Ile Pro Ser Ala Glu Asn Lys Asp Glu Ser Val Leu Asp Glu Phe
            100                 105                 110 tac cgt tta aat aga aaa gat cca agt ttc gca aag act cgt gtc att     384
Tyr Arg Leu Asn Arg Lys Asp Pro Ser Phe Ala Lys Thr Arg Val Ile
        115                 120                 125 gtt aac cgc gga cat gaa ctt cca act gac ggt caa tta ctt ctt act     432
Val Asn Arg Gly His Glu Leu Pro Thr Asp Gly Gln Leu Leu Leu Thr
    130                 135                 140 ccc aag gct gtt aaa gaa att att gat ctt tgc tta act cct gaa aaa     480
Pro Lys Ala Val Lys Glu Ile Ile Asp Leu Cys Leu Thr Pro Glu Lys
145                 150                 155                 160 gat tta caa aat aaa aaa att aat gaa gtc ttt agt aaa gaa ttt ttt     528
```

```
                 Asp Leu Gln Asn Lys Lys Ile Asn Glu Val Phe Ser Lys Glu Phe Phe
                                 165                 170                 175 gaa tca aac ttc tgg ctt tac tgg tca acg atg ttt gcc ttt gag cca             576
Glu Ser Asn Phe Trp Leu Tyr Trp Ser Thr Met Phe Ala Phe Glu Pro
            180                 185                 190 tgg gca agt gcg atg gaa atg cgt cgt tac tta atg cgt ttt gtt caa             624
Trp Ala Ser Ala Met Glu Met Arg Arg Tyr Leu Met Arg Phe Val Gln
                195                 200                 205 cac gtt tct aca ctt aag aat tta tca tca cta cgc ttt act aag tat             672
His Val Ser Thr Leu Lys Asn Leu Ser Ser Leu Arg Phe Thr Lys Tyr
        210                 215                 220 aac caa tat gaa tca tta att tta cca atg gtt aaa tac ttg aaa gat             720
Asn Gln Tyr Glu Ser Leu Ile Leu Pro Met Val Lys Tyr Leu Lys Asp
225                 230                 235                 240 cgc ggc gtg caa ttc cat tac aac acc gtt gtt gat aat atc ttt gtt             768
Arg Gly Val Gln Phe His Tyr Asn Thr Val Val Asp Asn Ile Phe Val
                245                 250                 255 aac cgt tca aat ggt gaa aag att gct aag caa att ctt tta act gaa             816
Asn Arg Ser Asn Gly Glu Lys Ile Ala Lys Gln Ile Leu Leu Thr Glu
            260                 265                 270 aac ggt gaa aaa aag agc atc gat tta aca gaa aat gac ctc gtc ttc             864
Asn Gly Glu Lys Lys Ser Ile Asp Leu Thr Glu Asn Asp Leu Val Phe
        275                 280                 285 gtt act aac ggt tca att act gaa agt aca act tat ggt gat aac ttg             912
Val Thr Asn Gly Ser Ile Thr Glu Ser Thr Thr Tyr Gly Asp Asn Leu
    290                 295                 300 cac cca gct tct gag gaa cat aaa tta ggt gct act tgg aaa tta tgg             960
His Pro Ala Ser Glu Glu His Lys Leu Gly Ala Thr Trp Lys Leu Trp
305                 310                 315                 320 caa aac ttg gca gcg caa gat gat gac ttc ggt cac cca gat gtc ttc            1008
Gln Asn Leu Ala Ala Gln Asp Asp Asp Phe Gly His Pro Asp Val Phe
                325                 330                 335 tgc aag gat att cca aag gct aac tgg gta atg tct gct aca att act            1056
Cys Lys Asp Ile Pro Lys Ala Asn Trp Val Met Ser Ala Thr Ile Thr
            340                 345                 350 ttt aag aat aat gat att gtg cca ttc att gaa gca gtt aat aag aag            1104
Phe Lys Asn Asn Asp Ile Val Pro Phe Ile Glu Ala Val Asn Lys Lys
        355                 360                 365 gat cca cac agc ggc tca att gta act agt ggg cct act acg att aag            1152
Asp Pro His Ser Gly Ser Ile Val Thr Ser Gly Pro Thr Thr Ile Lys
    370                 375                 380 gat tct aac tgg cta ctt ggt tat tca atc agt cgt cag cct cac ttt            1200
Asp Ser Asn Trp Leu Leu Gly Tyr Ser Ile Ser Arg Gln Pro His Phe
385                 390                 395                 400 gaa gca caa aag cct aac gaa ttg att gta tgg ctt tat ggt ttg ttc            1248
Glu Ala Gln Lys Pro Asn Glu Leu Ile Val Trp Leu Tyr Gly Leu Phe
                405                 410                 415 tca gac acc aaa ggt aac tat gtt gaa aag act atg cct gac tgt aac            1296
Ser Asp Thr Lys Gly Asn Tyr Val Glu Lys Thr Met Pro Asp Cys Asn
            420                 425                 430 ggt att gaa tta tgt gaa gaa tgg ctt tac cac atg ggt gtt cct gaa            1344
Gly Ile Glu Leu Cys Glu Glu Trp Leu Tyr His Met Gly Val Pro Glu
        435                 440                 445 gaa aga atc cca gaa atg gct tca gct gct acg act att cca gca cac            1392
Glu Arg Ile Pro Glu Met Ala Ser Ala Ala Thr Thr Ile Pro Ala His
    450                 455                 460 atg cca tat att act tca tac ttc atg cca aga gca tta ggc gac aga            1440
Met Pro Tyr Ile Thr Ser Tyr Phe Met Pro Arg Ala Leu Gly Asp Arg
465                 470                 475                 480
```

```
ccc aag gtt gtg cca gac cac tca aag aac ttg gcc ttc att ggt aac      1488
Pro Lys Val Val Pro Asp His Ser Lys Asn Leu Ala Phe Ile Gly Asn
            485                 490                 495 ttt gct gaa acg cca aga gac act gtc ttt acc act gaa tac tct gtc      1536
Phe Ala Glu Thr Pro Arg Asp Thr Val Phe Thr Thr Glu Tyr Ser Val
        500                 505                 510 aga act gcg atg gaa gct gta tac acc ttg ctt aac att gat cgt ggt      1584
Arg Thr Ala Met Glu Ala Val Tyr Thr Leu Leu Asn Ile Asp Arg Gly
    515                 520                 525 gtg cca gaa gta ttt gca tct gcc ttc gat gtc aga atg ctc atg aac      1632
Val Pro Glu Val Phe Ala Ser Ala Phe Asp Val Arg Met Leu Met Asn
530                 535                 540 gca atg tac tac ttg aat gat caa aag aag ctt gaa gat ctt gat ttg      1680
Ala Met Tyr Tyr Leu Asn Asp Gln Lys Lys Leu Glu Asp Leu Asp Leu
545                 550                 555                 560 cct att gct gaa aag ttg gca att aag ggg atg ctc aag aaa gtt aag      1728
Pro Ile Ala Glu Lys Leu Ala Ile Lys Gly Met Leu Lys Lys Val Lys
                565                 570                 575 ggc act tat ata gag gaa ttg ctt aag aag tat aag ttg gtt tag          1773
Gly Thr Tyr Ile Glu Glu Leu Leu Lys Lys Tyr Lys Leu Val
                580                 585                 590

<210> SEQ ID NO 2
<211> LENGTH: 590
<212> TYPE: PRT
<213> ORGANISM: Lactobacillus acidophilus

<400> SEQUENCE: 2

Met His Tyr Ser Ser Gly Asn Tyr Glu Ala Phe Val Asn Ala Ser Lys
1               5                   10                  15

Pro Lys Asp Val Asp Gln Lys Ser Ala Tyr Leu Val Gly Ser Gly Leu
            20                  25                  30

Ala Ser Leu Ala Ser Ala Val Phe Leu Ile Arg Asp Gly His Met Lys
        35                  40                  45

Gly Asp Arg Ile His Ile Leu Glu Glu Leu Ser Leu Pro Gly Gly Ser
    50                  55                  60

Met Asp Gly Ile Tyr Asn Lys Gln Lys Glu Ser Tyr Ile Ile Arg Gly
65                  70                  75                  80

Gly Arg Glu Met Glu Ala His Phe Glu Cys Leu Trp Asp Leu Phe Arg
                85                  90                  95

Ser Ile Pro Ser Ala Glu Asn Lys Asp Glu Ser Val Leu Asp Glu Phe
            100                 105                 110

Tyr Arg Leu Asn Arg Lys Asp Pro Ser Phe Ala Lys Thr Arg Val Ile
        115                 120                 125

Val Asn Arg Gly His Glu Leu Pro Thr Asp Gly Gln Leu Leu Leu Thr
    130                 135                 140

Pro Lys Ala Val Lys Glu Ile Ile Asp Leu Cys Leu Thr Pro Glu Lys
145                 150                 155                 160

Asp Leu Gln Asn Lys Lys Ile Asn Glu Val Phe Ser Lys Glu Phe Phe
                165                 170                 175

Glu Ser Asn Phe Trp Leu Tyr Trp Ser Thr Met Phe Ala Phe Glu Pro
            180                 185                 190

Trp Ala Ser Ala Met Glu Met Arg Arg Tyr Leu Met Arg Phe Val Gln
        195                 200                 205

His Val Ser Thr Leu Lys Asn Leu Ser Ser Leu Arg Phe Thr Lys Tyr
    210                 215                 220

Asn Gln Tyr Glu Ser Leu Ile Leu Pro Met Val Lys Tyr Leu Lys Asp
```

```
                225                 230                 235                 240

Arg Gly Val Gln Phe His Tyr Asn Thr Val Asp Asn Ile Phe Val
                            245                 250                 255

Asn Arg Ser Asn Gly Glu Lys Ile Ala Lys Gln Ile Leu Leu Thr Glu
                        260                 265                 270

Asn Gly Glu Lys Lys Ser Ile Asp Leu Thr Glu Asn Asp Leu Val Phe
                    275                 280                 285

Val Thr Asn Gly Ser Ile Thr Glu Ser Thr Thr Tyr Gly Asp Asn Leu
                    290                 295                 300

His Pro Ala Ser Glu Glu His Lys Leu Gly Ala Thr Trp Lys Leu Trp
        305                 310                 315                 320

Gln Asn Leu Ala Ala Gln Asp Asp Phe Gly His Pro Asp Val Phe
                        325                 330                 335

Cys Lys Asp Ile Pro Lys Ala Asn Trp Val Met Ser Ala Thr Ile Thr
                        340                 345                 350

Phe Lys Asn Asn Asp Ile Val Pro Phe Ile Glu Ala Val Asn Lys Lys
                        355                 360                 365

Asp Pro His Ser Gly Ser Ile Val Thr Ser Gly Pro Thr Thr Ile Lys
                370                 375                 380

Asp Ser Asn Trp Leu Leu Gly Tyr Ser Ile Ser Arg Gln Pro His Phe
        385                 390                 395                 400

Glu Ala Gln Lys Pro Asn Glu Leu Ile Val Trp Leu Tyr Gly Leu Phe
                        405                 410                 415

Ser Asp Thr Lys Gly Asn Tyr Val Glu Lys Thr Met Pro Asp Cys Asn
                        420                 425                 430

Gly Ile Glu Leu Cys Glu Glu Trp Leu Tyr His Met Gly Val Pro Glu
                        435                 440                 445

Glu Arg Ile Pro Glu Met Ala Ser Ala Thr Thr Ile Pro Ala His
                450                 455                 460

Met Pro Tyr Ile Thr Ser Tyr Phe Met Pro Arg Ala Leu Gly Asp Arg
        465                 470                 475                 480

Pro Lys Val Val Pro Asp His Ser Lys Asn Leu Ala Phe Ile Gly Asn
                            485                 490                 495

Phe Ala Glu Thr Pro Arg Asp Thr Val Phe Thr Thr Glu Tyr Ser Val
                        500                 505                 510

Arg Thr Ala Met Glu Ala Val Tyr Thr Leu Leu Asn Ile Asp Arg Gly
                        515                 520                 525

Val Pro Glu Val Phe Ala Ser Ala Phe Asp Val Arg Met Leu Met Asn
                    530                 535                 540

Ala Met Tyr Tyr Leu Asn Asp Gln Lys Lys Leu Glu Asp Leu Asp Leu
        545                 550                 555                 560

Pro Ile Ala Glu Lys Leu Ala Ile Lys Gly Met Leu Lys Lys Val Lys
                            565                 570                 575

Gly Thr Tyr Ile Glu Glu Leu Leu Lys Lys Tyr Lys Leu Val
                        580                 585                 590
```